(12) United States Patent
Covey

(10) Patent No.: US 6,844,456 B2
(45) Date of Patent: Jan. 18, 2005

(54) MODIFIED, HYDROXY-SUBSTITUTED AROMATIC STRUCTURES HAVING CYTOPROTECTIVE ACTIVITY

(75) Inventor: Douglas F. Covey, Ballwin, MO (US)

(73) Assignee: Washington University, St. Louis, MO (US)

( * ) Notice: Subject to any disclaimer, the term of this patent is extended or adjusted under 35 U.S.C. 154(b) by 215 days.

(21) Appl. No.: 10/007,450

(22) Filed: Nov. 5, 2001

(65) Prior Publication Data

US 2002/0103178 A1 Aug. 1, 2002

Related U.S. Application Data

(60) Provisional application No. 60/245,791, filed on Nov. 3, 2000.

(51) Int. Cl.$^7$ .............................. C07J 9/00; A61K 31/56

(52) U.S. Cl. .................. 552/545; 514/180; 552/502

(58) Field of Search .................................. 552/545, 502, 552/630, 610, 626; 514/180, 18.2

(56) References Cited

U.S. PATENT DOCUMENTS

| | | | |
|---|---|---|---|
| 3,472,885 A | 10/1969 | Bucourt et al. |
| 4,330,540 A | 5/1982 | Zeelen |
| 4,617,298 A | 10/1986 | Bodor et al. |
| 4,786,647 A | 11/1988 | Simpkins et al. |
| 5,552,395 A | 9/1996 | Gemmill, Jr. et al. |
| 5,554,601 A | 9/1996 | Simpkins et al. |
| 5,554,604 A | 9/1996 | Bonfils et al. |
| 5,679,668 A | 10/1997 | Bonfils et al. |
| 5,824,672 A | 10/1998 | Simpkins et al. |
| 5,843,934 A | 12/1998 | Simpkins |
| 5,859,001 A | 1/1999 | Simpkins et al. |
| 5,877,169 A | 3/1999 | Simpkins |
| 5,914,325 A | 6/1999 | Droescher et al. |
| 5,939,407 A | 8/1999 | Landfield |
| 5,972,923 A | 10/1999 | Simpkins et al. |
| 6,080,735 A | 6/2000 | Schwartz et al. |
| 6,172,056 B1 | 1/2001 | Droescher et al. |
| 6,197,833 B1 | 3/2001 | Simpkins et al. |
| 6,207,658 B1 | 3/2001 | Simpkins et al. |
| 6,245,756 B1 | 6/2001 | Patchev et al. |
| 6,265,147 B1 | 7/2001 | Mobley et al. |
| 6,436,917 B1 | 8/2002 | Droescher et al. |

FOREIGN PATENT DOCUMENTS

| | | |
|---|---|---|
| CA | 1 167 837 | 5/1984 |
| DE | 199 17 930 A1 | 10/2000 |
| EP | 0 069 424 B1 | 1/1983 |
| GB | 1 298 587 | 12/1972 |
| WO | WO 95/13076 A1 | 5/1995 |
| WO | WO 97/03661 A1 | 2/1997 |
| WO | WO 99/26630 A1 | 6/1999 |
| WO | WO 00/63228 A1 | 10/2000 |
| WO | WO 01/10430 A2 | 2/2001 |

OTHER PUBLICATIONS

P.S. Green et al. "ENT–Estradiol Exerts Neuroprotective Effects in vitro and in vivo" Society for Neuroscience Abstracts, vol. 25, No. 1/2 (Oct. 23, 1999) p. 1849.

C. Behl et al. "Neuroprotection against oxidative stress by estrogens: structure–activity relationship" Molecular Pharmacology, vol. 51, No. 4 (1997) pp. 535–541.

Ismail et al. "Synthesis and Biological Evaluation of Some Novel 2–(pyrimidin–4–yl)estradiol Derivatives" Eur. J. Med. Chem., vol. 30, No. 5 (1995) pp. 423–427.

Omar et al. "Synthesis, Binding Affinities and Uterotrophic Activity of Some 2–Substituted Estradiol and Ring–A–Fused Pyrone Derivatives" Eur. J. Med. Chem., vol. 29, No. 1 (1994) pp. 25–32.

Akhter et al., Saftey Study of Tirilazad Mesylate in Patients With Acute Ischmeic Stroke (STIPAS) Stroke, vol. 25, No. 2 (1994) p. 418–423.

A. Allais et al. "3–(β–Dialkylaminoethoxy)estra–1,3,5(10)–trienes" Chemical Abstracts, vol. 70, No. 25; Abstract No. 115418e (1969) p. 381.

K. Barnikol–Oettler et al. "Preparation of Estradiol 3–methyl Ether" Chemical Abstracts, vol. 160, No. 25, Abstract No. 106:214199c (1987).

C. Behl et al. "17–βEstradiol Protects Neurons from Oxidative Stress–Induced Cell Death in vitro" Biochemical and Biophysical Research Communications, vol. 216, No. 2 (1995) pp. 473–482.

G.C. Buzby et al. "Totally Synthetic Steriod Hormones. XIII. The Chemical Resolution of Some Racemic Estrane, 13β–Ethylgonane, and 13β–n–Propylgonane Derivatives and the Preparation of Some Estrane and 13β–Ethylgonne Derivatives of Unnatural Configuration" Journal of Medicinal Chemistry, vol. 10 (1967) pp. 199–204.

T. Fan et al. "ZYC–13, the enantiomer of 1,3,5(10)–estratriene 3–OL, exerts neuroprotective effects in vitro and in vivo" Presented at the 26th Soc. for Neuroscience Meeting, Nov. 4, 2000 to Nov. 9, 2000.

Y. Goodman et al. "Estrogens Attenuate and Corticosterone Exacerbates Excitotoxicity, Oxidative Injury, and Amyloid β–Peptide Toxicity in Hippocampal Neurons" Journal of Neurochemistry, vol. 66, No. 5 (1996) pp. 1836–1844.

(List continued on next page.)

*Primary Examiner*—Sabiha Qazi
(74) *Attorney, Agent, or Firm*—Senniger Powers

(57) ABSTRACT

The present invention is directed to modified, hydroxy-bearing aromatic ring structures having cytoprotective activity. More specifically, in a first embodiment the present invention is directed to phenolic compounds, and in particular steriods (e.g., estrogens), wherein a non-fused polycyclic, hydrophobic substituent is attached to the hydroxy-substituted A-ring thereof. The present invention is further directed to a process for conferring cytoprotection to a population of cells involving the administration of the compound.

25 Claims, 7 Drawing Sheets

OTHER PUBLICATIONS

P. Green et al. "The Nonfeminizing Enantiomer of 17β–Estradiol Protective Effects in Neuronal Cultures and a Rat Model of Cerebral Ischemia" Endocrinology, vol. 142, No. 1 (2001) pp. 400–406.

Hall et al. "Sex Differences in Postischemic Neuronal Necrosis in Gerbils" j. Cer. Blood Flow Metab., vol. 11 (1991) p. 292–298.

H. Kaneko et al. "The Synthesis of 2– and 4–Alkoxymethylestrogenes" Chem. Pharm. Bull., vol. 12, No. 2 (1964) pp. 196–203.

M. A. Levitt et al. "Reduction of Infarct Size During Myocardial Ischemia and Reperfusion by Lazaroid U–74500A, a Nonglucocorticoid 21–Aminosteriod" J. of Cardiovascular Pharmacology, vol. 23, No. 1 (1994) pp. 136–140.

W. Lunn et al. "The Adamantyl Carbonium Ion as a Dehydrogenating Agent, its Reactions with Estrone" Tetrahedron Letters, vol. 24, No. 23 (1968) pp. 6773–6776.

C. Miller et al. "In vitro antioxidant effects of estrogens with a hindered 3–OH function on the copper–induced oxidation of low density lipoprotein" Steroids, vol. 61 (1996) pp. 305–308.

Mooradian "Antioxidant Properties of Steroids" J. Steroid Boichem. Molec. Biol., vol. 45, No. 6 (1993) pp. 509–511.

M. Nakano et al. "Novel and Potent Biological Antioxidants on Membrane Phospholipid Peroxidation: 2–Hydroxy Estrone and 2–Hydrox Estradiol" Bochemical and Biophycial Research Communications, vol. 142, No. 3 (1987) pp. 919–924.

E. Niki et al. "Antioxidants in Relation to Lipid Peroxidation" Chemistry and Physics of Lipids, vol. 44, Nos. 2–4 (1987) pp. 227–253.

T. Patton et al. "Estrogens. IV. The Synthesis of 2– and 4–Alkylestrones" Journal of Organic Chemistry, vol. 27, No. 3 (1962) pp. 910–914.

E. J. Perez et al. "762.7—Structure–Activity Relationship of Estratrienes Against Glutamate Toxicity in a Mouse Hippocampal Cell Line" Presented at the 26th Soc. for Neuroscience Meeting, Nov. 4, 2000 to Nov. 9, 2000.

L. Prokai et al. "Synthesis and Biological Evaluation of 17β–Alkoxyestra–1,3,5(10)–trienes as Potential Neuroprotectants Against Oxidative Stress" J. Med. Chem., vol. 44, No. 1 (2001) pp. 110–114.

W. Romer et al. "Novel estrogens and their radical scavenging effects, iron–chelating, and total antioxidative actives: 17α–substituted analogs of $\Delta^{9(11)}$–dehydro–17β–estradiol" Steroids, vol. 62 (1997) pp. 688–694.

W. Romer et al. "Novel "scavestrogens" and their radical scavenging effects, iron–chelating, and total antioxidative actives: $\Delta^{8,9}$–dehydro derivatives of 17–α–estradiol and 17β–estradiol" Steroids, vol. 62 (1997) pp. 304–310.

A.G. Schering, "Preparation of ent–steroids as Selectively Effective Estrogens" Chemical Abstracts, vol. 133, No. 21, Abstract No. 133:296594x (2000) p. 766–767.

A. Seelig et al. "A method to determine the ability of drugs to diffuse through the blood–brain barrier" Proc. Natl. Acad. Sci. USA, vol. 91 (1994) pp. 68–72.

L. Tietze et al. "Synthesis of new 16–spirosteroids" Steroids, vol. 59 (1994) pp. 305–309.

J. Wilson et al. "U83836E Reduces Secondary Brain Injury in a Rabbit Model of Cryogenic Trauma" Journal of Trauma, vol. 39, No. 3 (1995) pp. 473–479.

A. Wunderli et al. "Geometry of the Activated Complex of the Thermal and Charge–Induced Aromatic Para to Ortho Claisen Rearrangement" Helvetica Chimica Acta, vol. 56 (1973) pp. 989–1011.

S. Xia et al. "A Novel Estrogen Analog, Inactive at the Estrogen Receptor, is Neuroprotective" Presented at the 26th Soc. for Neuroscience Meeting, Nov. 4, 2000 to Nov. 9, 2000.

S–H. Yang et al. "Neuroprotective Effects of a Novel Non–Recptor Binding Estrogen Analogue During Stroke" Presented at the 26th Soc. for Neuroscience Meeting, Nov. 4, 2000 to Nov. 9, 2000.

P = H, Me, Et    Q = H, Me, Et    M = H, OH, OCH₃

Y = H, Me, Et    R₁₃ = H, Me, Et    R_z = H, OH, =O

US 6,844,456 B2

MODIFIED, HYDROXY-SUBSTITUTED AROMATIC STRUCTURES HAVING CYTOPROTECTIVE ACTIVITY

REFERENCE TO RELATED APPLICATION

This application claims priority from U.S. provisional application, Ser. No. 60/245,791, filed on Nov. 3, 2000, the entire contents of which are incorporated herein by reference.

BACKGROUND OF THE INVENTION

The present invention is generally directed to modified, hydroxy-substituted or hydroxy-bearing aromatic structures having cytoprotective activity, as well as to a treatment process involving the administration of an effective dosage thereof. More specifically, the present invention is directed to phenolic compounds or catecholic compounds which have been modified by the attachment of a non-fused polycyclic, hydrophobic substituent. Such compounds have been found to possess enhanced cytoprotective activity, as compared to their respective analogs which do not contain such a substituent. This activity may be conferred to a population of cells in a subject upon the administration of an effective dosage of the modified compound.

Cytodegenerative diseases are characterized by the dysfunction and death of cells, this dysfunction or death in the case of neurons leading to the loss of neurologic functions mediated by the brain, spinal cord and the peripheral nervous system. Examples of chronic neurodegenerative diseases include Alzheimer's disease, peripheral neuropathy (secondary to diabetes or chemotherapy treatment), multiple sclerosis, amyotrophic lateral sclerosis, Huntington's disease and Parkinson's disease, Creutzfeldt-Jakob disease and AIDs dementia. Normal brain aging is also associated with loss of normal neuronal function and may entail the depletion of certain neurons. Examples of acute neurodegenerative disease are stroke and multiple infarct dementia. Sudden loss of neurons may also characterize the brains of patients with epilepsy and those that suffer hypoglycemic insults and traumatic injury of the brain, peripheral nerves or spinal cord.

There continues to be a need for treatments that protect cells from cell death resulting from episodes of, for example, disease, trauma, isolation and removal of tissues or cells from the body, or exposure to toxins. This need extends to, among other things: (i) treatments for nerve cell loss associated with chronic or acute neurodegenerative disorders or trauma; (ii) treatments to minimize tissue damage resulting from ischemia where ischemia may occur as a result of stroke, heart disease, a transplantation event, or other event resulting in a cut-off in nutritional supply to tissues; and, (iii) treatments to modulate cell death associated with other degenerative conditions (such as osteoporosis or anemia). The absence of an effective cytoprotective therapy can result in either loss of life or a general decline in the quality of life, including permanent disability with high health care costs to patients, their families and the health care providers.

There have been a number of experimental approaches and targets evaluated to develop drugs for the protection of cells from degeneration. Glutamate, the main excitatory neurotransmitter in the central nervous system, is necessary for many normal neurological functions, including learning and memory. Overactivation of glutamate receptors, however, results in excitotoxic neuronal injury, has been implicated in the pathogenesis of neuronal loss in the central nervous system (CNS) following several acute insults, including hypoxia/ischemia. During brain ischemia caused by stroke or traumatic injury, excessive amounts of the excitatory amino acid glutamate are released from damaged or oxygen deprived neurons. This excess glutamate binds to the N-methyl-D-aspartate (NMDA) receptor which opens the ligand-gated ion channel thereby allowing calcium influx, producing a high level of intracellular calcium which activates biochemical cascades resulting in protein, DNA, and membrane degradation leading to cell death. This phenomenon, known as excitotoxicity, is also thought to be responsible for the neurological damage associated with other disorders ranging from hypoglycemia and cardiac arrest to epilepsy. In addition, there are preliminary reports indicating similar involvement in the chronic neurodegeneration of Huntington's, Parkinson's and Alzheimer's diseases. Accordingly, many pharmaceutical strategies have been assessed which aim to decrease levels of glutamate excess.

Oxidative stress, caused by reactive oxygen species, represents another injury mechanism implicated in many of the same acute and chronic diseases. Reactive oxygen species (e.g., superoxide radical) would cause oxidative damage to cellular components, such as peroxidation of cell membrane lipids, inactivation of transport proteins, and inhibition of energy production by mitochondria.

Glutamate excitotoxicity and oxidative stress, may be interlinked; reactive oxygen species formation may occur as a direct consequence of glutamate receptor overstimulation and thus mediate a component of glutamate. Excitotoxicity, in turn, can be reduced by free radical scavengers, including C, Zn-superoxide dismutase, the 21-aminosteroid "lazaroids", the vitamin E analog, trolox, spin-trapping agents such as phenylbutyl-N-nitrone, and the ubiquinone analog, idebenone which reduce the amount of reactive oxygen species.

Mooradian has reported that certain estrogens have significant anti-oxidant properties in in vitro biochemical assays, but that this effect is not seen with all estrogens. (See, J. Steroid Biochem. Molec. Biol., 45 (1993) 509–511.) Because of the variation in anti-oxidant properties noted by Mooradian in his biochemical assays, he concluded steroid molecules must have certain anti-oxidant determinants which were as yet unknown. Similar observations concerning steroids with phenolic A rings were reported in PCT Patent Application No. WO 95/13076, wherein biochemical assays were used to show anti-oxidant activity. However, the assays used by Mooradian, as well as those used in WO 95/13076, were biochemical assays and, as such, did not directly examine the effects of these molecules on cells. In contrast, Simpkins et al. describe, in U.S. Pat. No. 5,554,601 for example, cell-based assays to determine a method of conferring neuroprotection on a population of cells using estrogen compounds based on demonstrated cell protective effects. As a result, in recent years it has become recognized that estrogen, as well as other polycyclic phenols, may be used for this purpose. (See, e.g., U.S. Pat. Nos. 5,972,923; 5,877,169; 5,859,001; 5,843,934; 5,824,672; and, 5,554,601; all of which are incorporated herein by reference.)

The mechanism by which estrogen compounds bring about a neuroprotective effect is still not fully understood. However, these compounds have been shown to have a number of different physiological and biochemical effects on neurons. For example, estrogen has been shown to stimulate the production of neurotrophic agents that in turn stimulate neuronal growth. Estrogen compounds have also been found to inhibit NMDA-induced cell death in primary neuronal cultures (see, e.g., Behl et al. Biochem. Biophys Res.

Commun. (1995) 216:973; Goodman et al. J. Neurochem. (1996) 66:1836), and further to be capable of removing oxygen free radicals and inhibiting lipid peroxidation (see, e.g., Droescher et al. WO 95/13076). For example, Droescher et al. describe cell free in vitro assay systems using lipid peroxidation as an endpoint in which several estrogens, as well as vitamin E, were shown to have activity. Estradiol has also been reported to reduce lipid peroxidation of membranes (see, e.g., Niki (1987) Chem. Phys. Lipids 44:227; Nakano et al. Biochem. Biophys. Res. Comm. (1987) 142:919; Hall et al. J. Cer. Blood Flow Metab. (1991)11:292). Other compounds, including certain 21-amino steroids and a glucocorticosteroid, have been found to act as anti-oxidants and have been examined for their use in spinal cord injury, as well as head trauma, ischemia and stroke. (See, e.g., Wilson et al. (1995) J. Trauma 39:473; Levitt et al. (1994) J. Cardiovasc. Pharmacol 23:136; Akhter et al. (1994) Stroke 25; 418).

While anti-oxidant behavior is believed to be an important property, a number of other factors are believed to be involved in achieving neuroprotection. As a result, it is to be noted that therapeutic agents selected on the basis of a single biochemical mechanism may have limited generalized utility in treating disease or trauma in patients. For example, in order to achieve an anti-oxidant effect in vitro using estrogen, Droescher et al. used very high doses of estrogens. Such doses, even if effective on neurons in vivo, would have limited utility in treating chronic neurological conditions because of associated problems of toxicity that result from the prolonged use of these high dosages.

In addition to the issues related to compound toxicity, consideration must also be given to the ability of a particular compound to reach the target site, which in some applications is controlled by the ability of the compound to cross the blood-brain barrier. The blood-brain barrier is a complex of morphological and enzymatic components that retards the passage of both large and small charged molecules, and thus limits the access of such molecules to cells of the brain. Furthermore, not only must the compound be capable of reaching the target site, but it must also do so in a state or configuration which enables it to carry-out its designated function.

In view of the foregoing, it can be seen that a need continues to exist for the identification of compounds which have demonstrated biological efficacy in protecting humans from the consequences of abnormal cell death in body tissue; compounds which are capable of crossing the blood-brain barrier and which are suitable for administration in dosages which are non-toxic. This identification requires continuing advances in the understanding of the structural requirements for compositions capable of inducing neuroprotection, which in turn provide the basis for designing novel drugs that have enhanced cytoprotective properties while at the same time have reduced adverse side effects.

SUMMARY OF THE INVENTION

Among the several objects and features of the present invention include the provision of a process treating a population of cells against cell death or cell damage wherein an effective dose of such a cytoprotective or neuroprotective compound is administered thereto, the compound having a hydroxy-substituted aromatic ring structure modified by, in some embodiments, (i) a non-fused polycyclic, hydrophobic substituent, or (ii) a bridged structure, a spiro structure (attached via a linker) or a ring assembly; and, the provision of a process for treating a cytodegenerative or neurodegenerative disease wherein an effective dose of such a compound is administered.

Further among the several objects and features of the present invention is the provision of a compound having a hydroxy-substituted aromatic ring structure modified as described above, and in some cases being further modified by at least one other non-hydrogen substituent, the compound having cytoprotective or neuroprotective activity; and, the provision of such a compound wherein the hydroxy-substituted, aromatic ring structure is also polycyclic.

Briefly, therefore, the present invention is directed to a process for conferring cytoprotection on a population of cells which comprises administering to that population of cells a compound comprising a hydroxy-substituted aromatic ring structure and a non-fused polycyclic, hydrophobic substituent attached thereto. The present invention is further directed to such a process wherein the cells are neurons.

The present invention is further directed to a process for treating a cytodegenerative disease comprising administering to a subject (e.g., human or animal) in need thereof such a compound, or a pharmaceutical composition comprising such a compound.

The present invention is still further directed to a compound having cytoprotective activity, the compound having the formula:

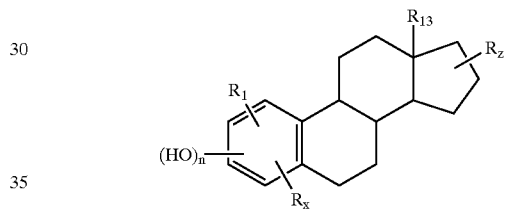

wherein: n is 1 or 2; $R^1$ is a non-fused polycyclic, hydrophobic substituent; $R^x$ is selected from the group consisting of hydrogen and substituted or unsubstituted alkyl; $R^{13}$ is hydrogen or substituted or unsubstituted alkyl; and, $R^z$ is hydrogen, hydroxy, substituted or unsubstituted alkyl, or oxo, with the proviso that when the compound has the following structure:

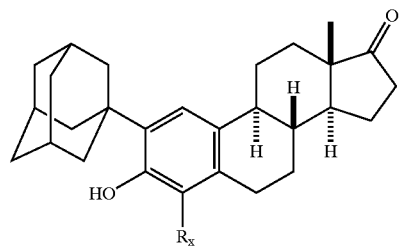

$R^x$ is not hydrogen.

Other objects and features of the present invention will be in part apparent and in part pointed out hereinafter.

DETAILED DESCRIPTION OF THE PREFERRED EMBODIMENTS

Figure 1A:
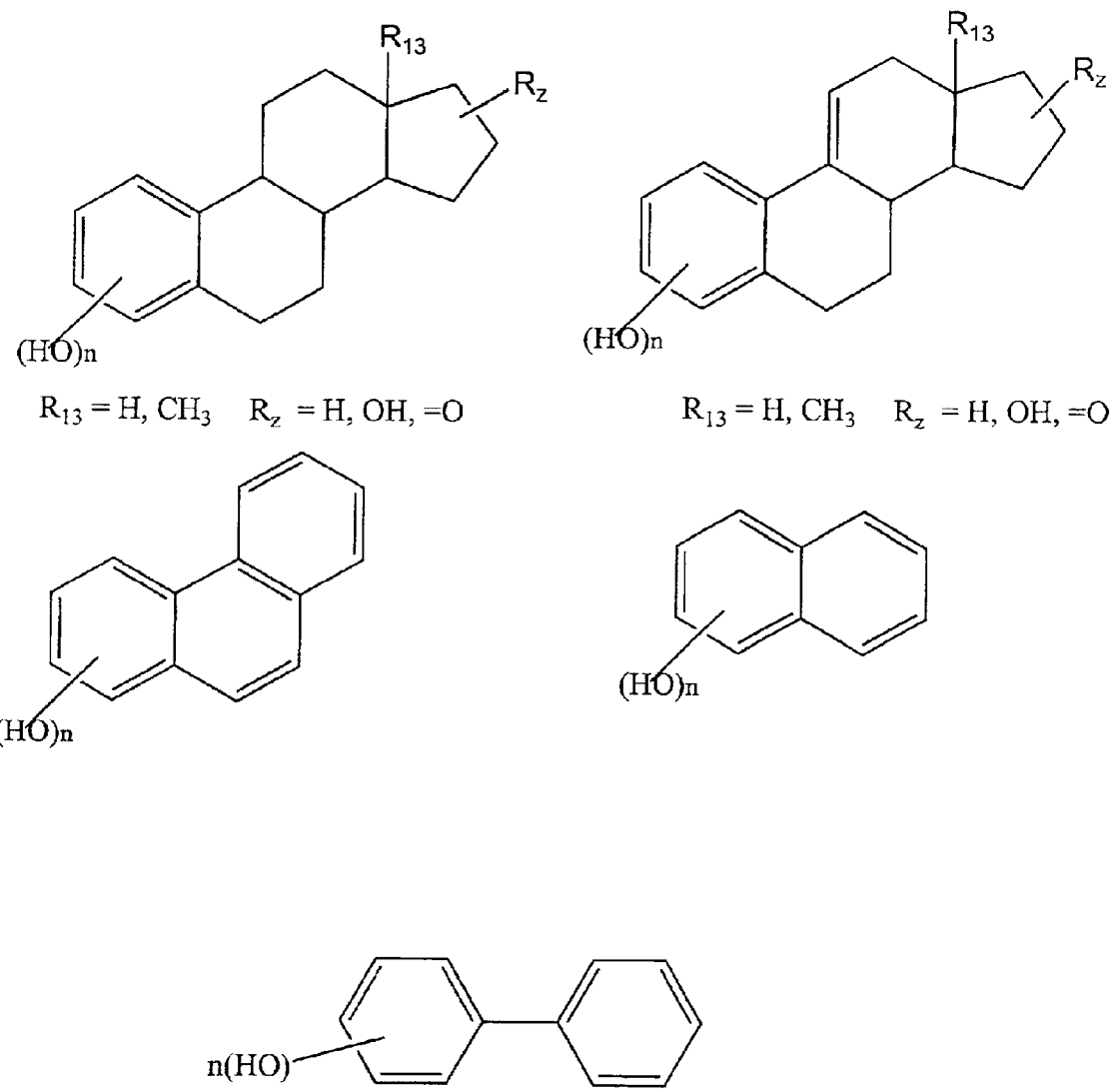
FIGS. 1A, 1B and 1C generally illustrate chemical structures of some preferred hydroxy-substituted aromatic compounds (e.g., phenols, catechols, etc., wherein n=1, 2 or more), which can be modified with a large, hydrophobic substituent as described herein in accordance with the present invention and which may be used to confer cytoprotection to a population of cells upon the administration of an effective dose thereof.

It is now recognized that certain polycyclic phenolic compounds, in particular estrogen-based compounds, have cytoprotective, and in some cases neuroprotective, activity (see, e.g., U.S. Pat. Nos. 5,972,923; 5,877,169; 5,859,001; 5,843,934; 5,824,672; 5,554,601; 6,197,833; and, 6,207,658; all of which are incorporated herein by reference). Without being held to a particular theory, it is generally believed that the activity associated with estrogen compounds is, at least in part, a result of the ability of estrogens, or more generally polycyclic phenolic compounds, because of their lipophilic nature, to become inserted into the cell membrane. Once in this position, the intact phenol group can donate a hydroxy hydrogen radical to prevent the cascade of membrane lipid peroxidation. Furthermore, it is generally believed that the significant potency of estrogens is because of their ability to donate a hydroxy hydrogen radical from several positions on the A ring (see, e.g., U.S. Pat. No. 5,972,923), and because a relatively stable, oxidized estrogen is formed as a result of this hydrogen radical donation (due to the effects of resonance stability).

Surprisingly, it has now been discovered that these compounds, as well as dihydroxy (e.g., catechol), trihydroxy, etc. analogs thereof, may be modified by means of attaching a large or bulky hydrophobic substituent on the hydroxy-substituted ring, or alternatively at some other position proximate to the hydroxy group, yielding compounds which are also capable of conferring cytoprotection to a population of cells (e.g., neurons). In fact, Applicant's experimental data suggests the addition of such substituents, such as for example bridged polycyclic substituents, can act to enhance the cytoprotective activity of these compounds, relative to their respective non-substituted analogs.

Modified Phenolic or Catecholic Compounds

As stated above, contrary to expectations, it has been discovered that previously reported phenolic compounds, as well as dihydroxy (e.g., catecholic) analogs thereof, can be modified by means of attaching a large, hydrophobic substituent (such as, for example, a polycyclic substituent comprising a bridged structure, a spiro structure attached via a linker, or a ring assembly), on or proximate to the hydroxy-bearing ring, in order to obtain a novel class of compounds having enhanced cytoprotective, and in some cases neuroprotective, activity. More specifically, it has been discovered that compounds having the formula (I):

$$X—R^1 \quad (I)$$

wherein X generally represents the core or central structure, which in one exemplary embodiment is a phenol (such as those disclosed in, for example, U.S. Pat. Nos. 5,972,923; 5,877,169; 5,859,001; 5,843,934; 5,824,672; 5,554,601; 6,197,833; and, 6,207,658; all of which are incorporated herein by reference) and in a second exemplary embodiment is a catechol (such as the dihydroxy analogs of those molecules disclosed in the aforementioned U.S. patents), to which the modifying hydrophobic substituent $R^1$ is attached, are suitable for use in treatments that protect a population of cells from cell death resulting from episodes of, for example, disease, trauma, isolation and removal of tissues or cells from the body, or exposure to toxins.

Generally speaking, the core structure, X, may represent essentially any compound possessing a hydroxy-substituted aromatic ring. In a first embodiment, X represents a compound having a terminal phenol ring while, in a second embodiment, X represents a compound having a terminal, dihydroxy-substituted (e.g. catechol) ring. More specifically, in these embodiments, the present invention is directed to compounds having the general formula (II)

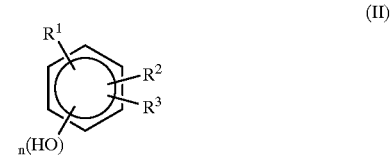

wherein: n=1 or 2, for the first and second embodiments respectively; $R^1$ is as previously noted and as further defined herein; and, $R^2$ and $R^3$ are hydrogen or some other substituent, also as further described herein (including wherein these two are bound to different carbon atoms on the hydroxy-substituted ring, these substituents and the carbon atoms to which they are bound forming a second, fused ring); X being generally represented by formula (III)

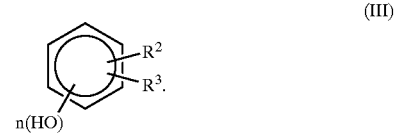

In this regard it is to be noted that, as further described herein, in alternative embodiments X represents a polycyclic compound; that is, X represents a compound having two or more (i.e., 2, 3, 4, 5 or more) hydrocarbon ring structures, or heterohydrocarbon ring structures (wherein a heteroatom is present in the ring), which may be fused or bound by some linkage, provided the terminal ring bears one or more hydroxy groups (e.g., phenol, catechol, etc.). In some particularly preferred embodiments, as further described herein, X may be a steroid-like structure.

Additionally, it is to be noted that such polycyclic compounds may optionally have a polar or hydrophilic substituent that is at or near the end which is essentially opposite the hydrophobic substituent, $R^1$, thus rendering the overall compound (i.e., X—$R^1$) amphipathic. Such polar or hydrophilic substituents include, for example, oxo and hydroxy, as well alkoxy or alkyloxy (wherein for example a hydroxy substituent has be used to form an ether or has been esterified, by means common in the art).

Figure 1B:
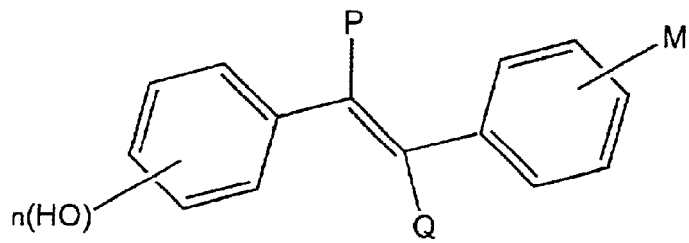
Figure 1C:
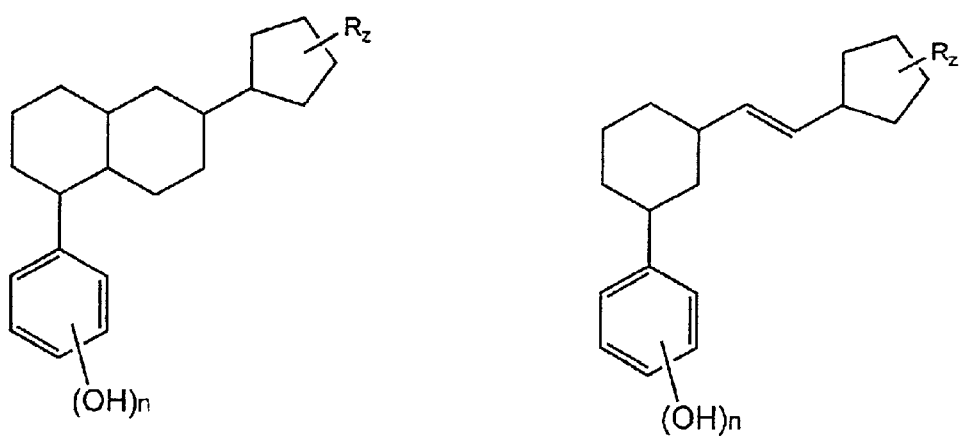
Figure 1C:
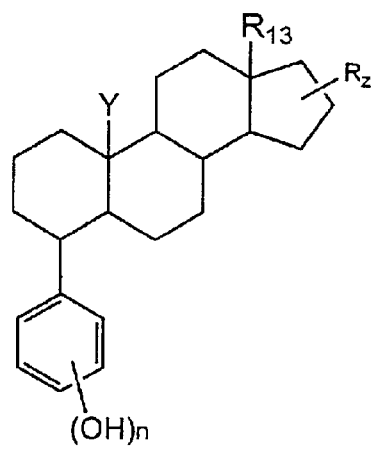

Referring now to FIGS. 1A, 1B and 1C, examples of core structure, X, suitable for use in the present invention include: (i) linked, two-ring structures such as stibesterols (e.g., dimethylstibesterol, diethylstibesterol, dimethylstibesterol-mono-O-methyl, and diethylstibesterol-mono-O-methyl); (ii) non-steroidal structures having a terminal hydroxy-bearing ring and at least two additional hydrocarbon ring structures, such as three-ring compounds (e.g., [2S-(2a,4aα,10αβ)]-1,2,3,4,4a,9,10,10a-octahydro-7-hydroxy-2-methyl-2-phenanthrenemethanol (PAM) and [2S-(2a,4aα,10αβ)]-1,2,3,4,4a,9,10,10a-octahydro-7-hydroxy-2-methyl-2-phenanthrenecarboxyaldehyde (PACA)); (iii) compounds having a terminal hydroxy-bearing ring and at least three additional carbon rings (e.g., 3,17α-estradiol; 3,17β-estradiol; estratriene-3-ol; 2-hydroxy-17α-estradiol; 2-hydroxy-17β-estradiol; estrone, 2-hydroxy estrone; estriol; 2-hydroxy estriol; ethynyl estradiol; and, 2-hydroxy ethynyl estradiol).

It is to be noted in this regard that the above-referenced listing of compounds is not intended to be exhaustive. For example, the position of the hydroxy group or groups on the terminal ring is not, in all cases, narrowly critical; that is, in some cases, the hydroxy group may occupy essentially any available position (which, depending upon the particular structure of X, may be the 1, 2, 3, 4, etc. position on the terminal ring). Additionally, in some cases, it may be favorable for X to contain additional double bonds in conjugation with the hydroxy-bearing aromatic ring (such as in the case of distilbesterol compounds), for example as in the case of polycyclic compounds having the general structure (IV):

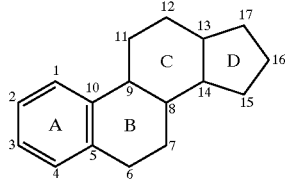

(IV)

wherein a carbon-carbon double bond is present between C-6 and C-7, C-8 and C-9, C-9 and C-11, or one of the possible combinations thereof.

Without being held to any particular theory, it is generally believed this additional conjugation is favorable because it allows for the formation of a more stable, oxidized form of the compound; that is, it allows for additional delocalization of the phenoxy radical, which is believed to be formed as a result of the loss of a hydrogen radical to quench hydroperoxides (formed by the interaction of oxygen radical species with unsaturated fatty acids). Accordingly, X may be other than herein described without departing from the scope of the present invention.

In accordance with the present invention, it has been discovered that the core structure, X, may be modified by the addition of one or more large, hydrophobic substituents, $R^1$, in order to achieve enhanced cytoprotective activity, relative to the non-substituted analogs thereof (as further discussed and illustrated herein). More specifically, it has been found that the cytoprotective activity of, for example, the above-described phenolic compounds (such as those described by Simpkins et al.), as well as the dihydroxy-analogs thereof, can be enhanced by the attachment of such a substituent either (i) on the terminal, hydroxy-bearing ring, or (ii) at some other position proximate the hydroxy group of the ring (see, e.g., FIG. 3). Furthermore, the hydrophobic substituent, $R^1$, can be attached directly or by some linkage (as further described herein; see also FIG. 3).

Figure 2A:
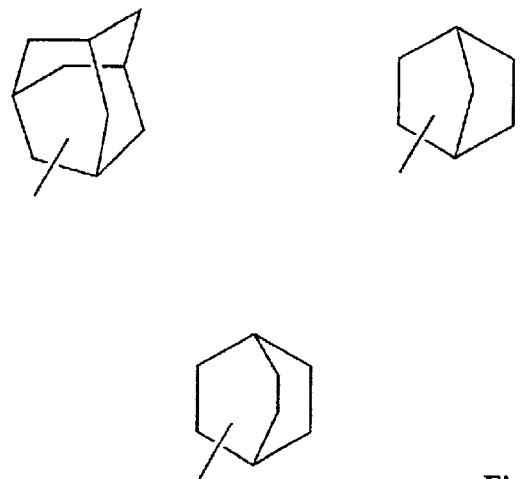
FIGS. 2A and 2B generally illustrate chemical structures of, in some embodiments, preferred polycyclic, hydrophobic substituents (e.g., bridged substituents), as well as some alternative hydrophobic substituents (e.g., bridge-containing or ring assembly substituents) suitable for use in the present invention.

Generally speaking, it has been found that enhanced cytoprotective activity is achieved when, in one embodiment, $R^1$ is a bridged polycyclic, hydrophobic substituent. Referring now to FIG. 2A, suitable substituents include, for example, bicyclic, tricyclic, tetracyclic, etc. structures comprising about 4, 6, 8, 10, 12 or more carbon atoms, such as: bicyclo [1.1.0]butanyl; bicyclo[2.2.1]heptanyl (i.e., norbornyl); bicyclo[3.2.1]octanyl; bicyclo [4.3.2]nonanyl; bicyclo[4.3.2]undecanyl; tricyclo[2.2.1.0$^1$] heptanyl; tricyclo[5.3.1.1$^1$]dodecanyl; tricyclo[3.3.1.13,7] decanyl (i.e., adamantyl); tricyclo[5.4.0.0$^{2,9}$]undecanyl; and, tricyclo[5.3.2.0$^{4,9}$] dodecanyl.

Without being held to a particular theory, this enhanced activity is believed to be, at least in part, a result of the hydrophobic substituent $R^1$ taking up a position within the void region of the cell membrane or lipid bilayer, thus acting to "anchor" the compound and orient it such that the hydroxy-bearing aromatic ring (e.g., phenol or catechol) is positioned proximate double bonds in the fatty acids of the lipid chains. The enhancement in the effectiveness or activity of the present compounds is therefore believed to be a result of the fact that, because of their composition and structure, these compounds are naturally positioned within the environment to which they are delivered at a location which optimizes their effectiveness.

Furthermore, it is generally believed that orientation of the present compounds within the lipid bilayer or cell membrane may be further aided, in some cases, by the addition or attachment of a polar or hydrophilic group at or near the end of the compound which is substantially opposite the end to which the hydrophobic substituent $R^1$ is attached. Other factors which may also impact orientation of the compound include: (i) a substantially planar core structure X, and additionally the entire compound, (which is believed to enhance the performance of the present compounds); and/or (ii) the absence of a polar or hydrophilic substituent ($R^2$, $R^3$, etc.) at a centrally located position on the compound (which is believed to detrimentally impact performance). For example, in the case of estrogen-like compounds, Applicant's experience to-date suggests changing the stereochemistry on the B or C ring by, for example, opening the B ring decreases activity, and the presence of a polar group on the B or C ring reduces activity as well.

Figure 2B:
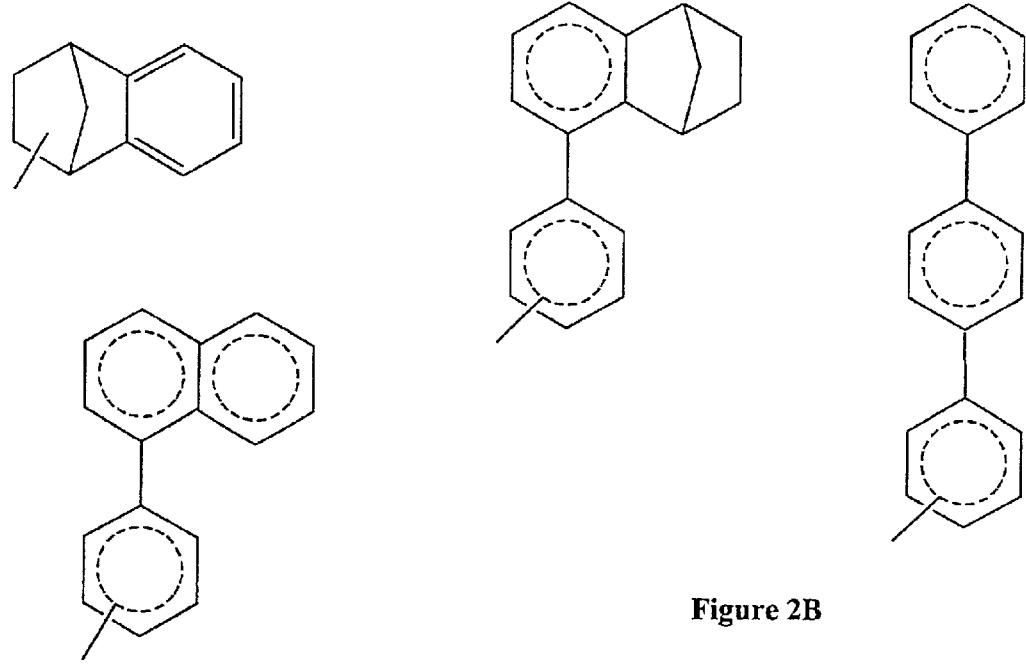

Accordingly, essentially any large, hydrophobic substituent which achieves the desired result (i.e., which acts to "anchor" the compound and orient it at an optimal position within the lipid bilayer or cell membrane) may be employed in accordance with the present invention. More specifically, it is generally believed that essentially any substituent may be employed provided it is: (i) sufficiently hydrophobic in nature, such that it will be "drawn" or "pulled" into the hydrophobic portion of the bilayer or membrane; (ii) sufficiently large, such that once in the hydrophobic region it disturbs fatty acids in the membrane, thus disrupting membrane integrity to a degree which results in the substituent being forced into the membrane void; and, (iii) sufficiently long, either by itself or by the use of a linker, such that the hydroxy-substituted ring is positioned proximate the fatty acid double bonds. Referring now to FIG. 2B, examples of suitable alternative embodiments of $R^1$ include non-planar, polycyclic substituents, such as bridged structures or ring assemblies, which may be used alone or which may additionally be fused with another ring structure.

With respect to the position of the hydroxy-substituted ring, it is to be noted that a typical membrane phospholipid has a length ranging from about 20 to about 30 Å (angstroms), as measured from about the end of the polar head group to about the end of the C-16 alkyl chain (by means of molecular modeling programs standard in the art). Accordingly, it is to be noted that in such cases essentially any combination of (i) a terminal hydroxy-bearing aromatic ring structure (e.g., phenol or catechol), and (ii) a hydrophobic substituent on or proximate to the hydroxy group on the aromatic ring structure, may be employed in the present invention, provided the distance between about the end of the hydrophobic "anchoring" substituent $R^1$ and about the opposite end of the hydroxy-bearing ring ranges from about 10 to less than about 30 Å (i.e., about 15 Å, 20 Å, 25 Å).

Figure 3:
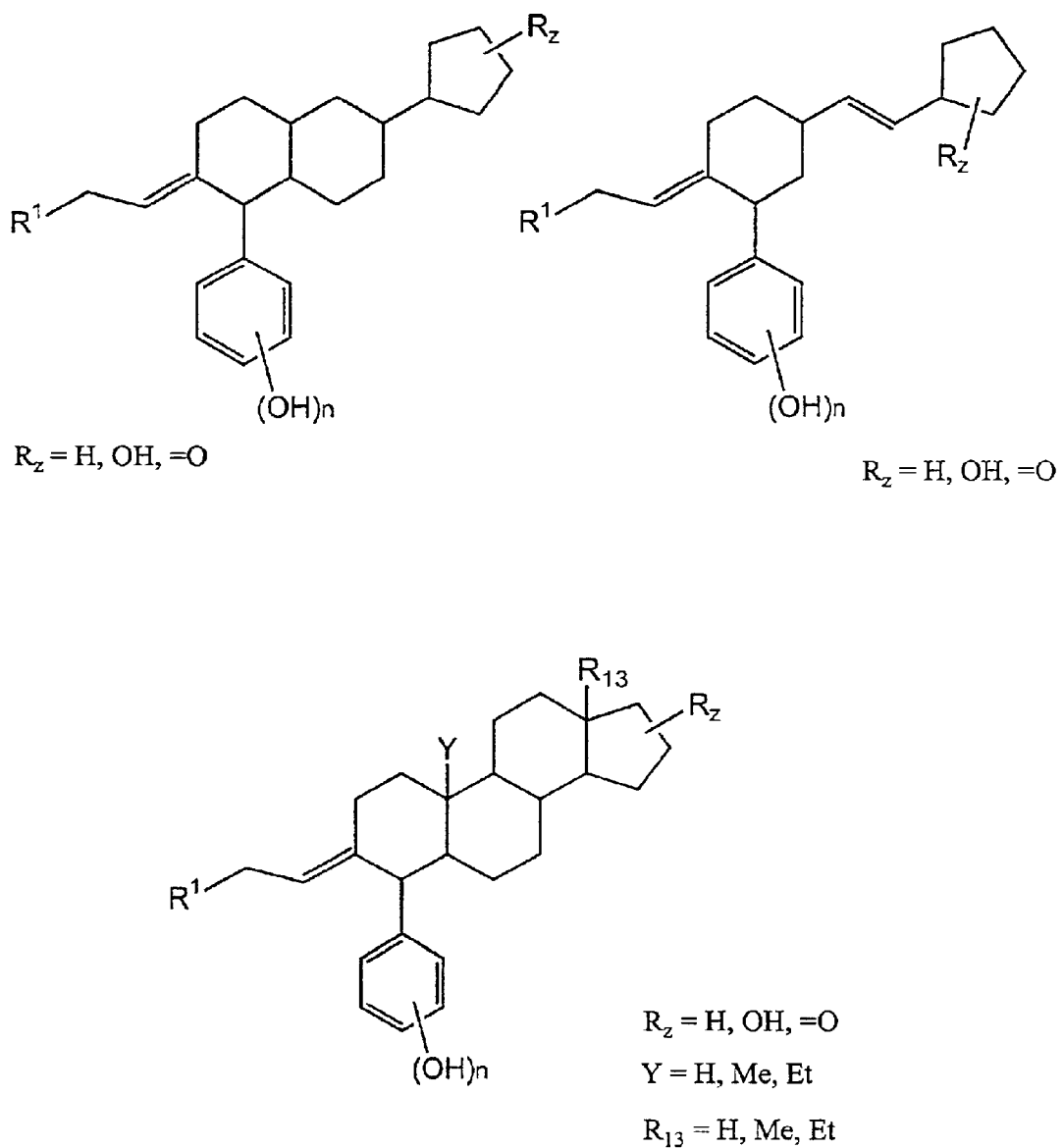
FIG. 3 generally illustrates chemical structures of some alternative hydroxy-substituted aromatic compounds (e.g., phenols, catechols, etc., wherein n=1, 2 or more) wherein the modifying substituent $R^1$ is not attached directed to the hydroxy-substituted aromatic ring, but rather is proximate to said ring, and further wherein said substituent $R^1$ is attached via a linker (e.g., alkenylene linker).

Referring now to FIG. 3, it is to be further noted that, as previously mentioned, while the "anchoring" substituent is typically attached directly to hydroxy-bearing aromatic ring, it may also be attached proximate this hydroxy group or groups; that is, the point of attachment of this substituent is not narrowly critical in all applications, provided that in such applications the point of attachment of the substituent is sufficient to orient the compound in such a way that the desired enhancement in activity is achieved. Accordingly, the substituent $R^1$ may be 1, 2, 3, 4 or more carbons from the hydroxy-bearing carbon, in some cases. Typically, however, the substituent $R^1$ will be adjacent or alpha to the hydroxy-bearing carbon. For example, in certain preferred embodiments, the hydroxy group is at a 2 or 3 position, which means $R^1$ is preferably in a 2, 3 or 4 position.

It is to be still further noted that, as illustrated below (as well as in FIG. 3), the anchoring substituent $R^1$ may be directly attached to the core molecule or it may alternatively be attached via a linker ("L"), provide the linker is of a length sufficient to generally position the hydroxy-bearing aromatic ring structure as described above.

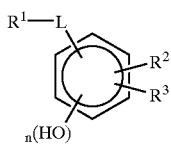

Typically, a hydrocarbylene linker (e.g., alkyl, akenyl, alkynyl) will be employed having a length ranging from about 1 to about 6 carbons in the main chain (e.g., methylene, ethylene, ethenylene, propylene, propenylene, etc.), with 1, 2 or 3 carbons in the main chain being preferred in some instances. Alternatively, however, in some embodiments, a hetero-substituted hydrocarbylene linker (such as an ether or thioether) may be employed.

Additional and/or Alternative Substitution

In addition to the presence of one or more hydrophobic substituents, $R^1$, as described herein, it is to be noted that one or more other substituents (e.g., $R^2$, $R^3$, $R^x$, etc.), which may be the same or different, may be attached to the hydroxy-bearing aromatic ring, or alternatively to some other segment or portion of the core structure X, provided the hydroxy-bearing ring remains in a substantially terminal position in the overall compound (i.e., X—$R^1$) structure; that is, it is to be noted that the present compound may optionally contain one or more additional substituents, which may be the same or different, at various available positions on the core structure, X, as illustrated below wherein X is a polycyclic structure (e.g., an estrogen derivative) having the formula (V):

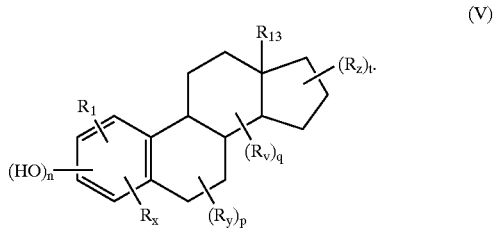

These other substituents (e.g., $R^y$, $R^v$, $R^z$) may, in some embodiments, be independently selected from the group consisting of hydrogen, substituted or unsubstituted hydrocarbyl (e.g., methyl, ethyl, propyl, propenyl, butyl, etc.), halogens (e.g., fluoro, bromo, chloro), amides, sulfates, and nitrates (wherein p, q and t generally represent the number of such substituents present on, in this case, the B, C and D rings respectively, and which typically range from 0 to 2 for the B and C rings, and 0 to 3 for the D ring).

Figure 4:
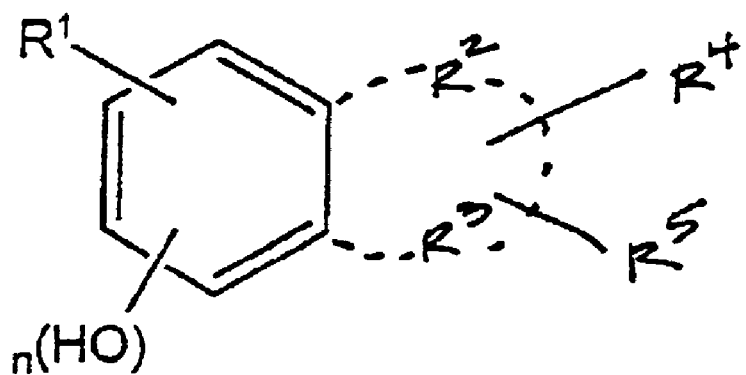
FIG. 4 generally illustrates certain embodiments of the compounds of the present invention, wherein other substituents (e.g., $R^2$, $R^3$, $R^4$, $R^5$, etc.) attached to the terminal hydroxy-substituted, aromatic ring are fused to form polycyclic ring structures (i.e., structures having 2, 3 or more rings, such as those illustrated in FIGS. 1A–1C).
Figure 4:
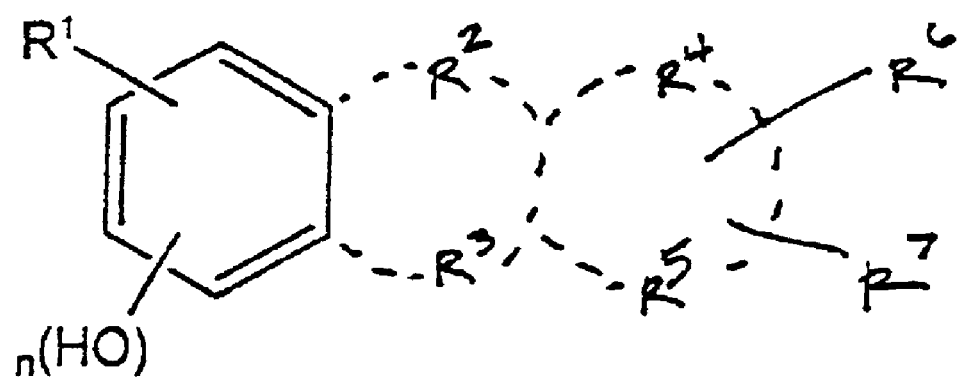

Furthermore, referring now to FIG. 4, as previously noted, the substituents (e.g., $R^2$ and $R^3$) may, in combination with the carbon atoms to which they are bound, form a second, fused ring (e.g., a 5, 6, 7, etc. membered hydrocarbyl or heterohydrocarbyl) structure with the terminal, hydroxy-bearing ring. This second ring may, in turn, be further substituted in the same way as described herein with reference to the terminal hydroxy-bearing ring; that is, the second ring may have one or more substituents (e.g., $R^4$, $R^5$, etc.) independently selected from the group provided for $R^2$ and $R^3$, which means X may in some embodiments comprise a third, forth, fifth, etc. ring structure (as shown, for example, in FIGS. 1A, 1B and 1C and as further described herein).

In some preferred embodiments, substituents $R^2$, $R^3$, $R^4$, $R^5$, etc., as well as $R^y$, $R^v$, $R^z$) may be, for example:

(a) Alkyl, alkenyl, alkynyl, containing up to about six carbon atoms in the main chain or ring structure (e.g., methyl, ethyl, propyl, butyl, pentyl, hexyl, dimethyl, isobutyl, isopentyl, tert-butyl, sec-butyl, methylpentyl, neopentyl, isohexyl, ethenyl, propenyl, butenyl, pentenyl, hexenyl, hexadienyl, 1,3-hexadiene-5-ynyl, isopropenyl, ethynyl, ethylidenyl, vinylidenyl, isopropylidenyl); sulfate; mercapto; methylthio; ethylthio; propylthio; methylsulfinyl; methylsulfonyl; thiohexanyl; thiopentyl; thiocyanato; sulfoethylamido; thionitrosyl; thiophosphoryl; p-toluenesulfonyl; amino; imino; cyano; carbamoyl; acetamido; hydroxyamino; nitroso; nitro; cyanato; selecyanato; arc-cosine; pyridinium; hydrazide; semicarbazone; carboxymethylamide; oxime; hydrazone; sulfurtrimethylammonium; semicarbazone; O-carboxymethyloxime; aldehyde hemiacetate; methylether; ethylether; propylether; butylether; benzylether; methylcarbonate; carboxylate; acetate; chloroacetate; trimethylacetate; cyclopentylpropionate; propionate; phenylpropionate; carboxylic acid methylether; formate; benzoate; butyrate; caprylate; cinnamate; decylate; heptylate; enanthate; glucosiduronate; succinate; hemisuccinate; palmitate; nonanoate; stearate; tosylate; valerate; valproate; decanoate; hexahydrobenzoate; laurate; myristate; phthalate; hydroxy; ethyleneketal; diethyleneketal; chloroformate; formyl; dichloroacetate; keto; difluoroacetate; ethoxycarbonyl; trichloroformate; hydroxymethylene; epoxy; peroxy; dimethyl ketal; acetonide; cyclohexyl; benzyl; phenyl; diphenyl; benzylidene; and, cyclopropyl. The substituent(s) may in some embodiments be attached to any of the constituent rings of X (i.e., the hydroxy-substituted ring or another ring bound or fused thereto) to form, for example, a pyridine, pyrazine, pyrimidine, or v-triazine. The substituent(s) may also include, for example, any of the six member or five member rings in section (b), below.

(b) A cyclic or heterocyclic carbon ring, which may be an aromatic or non-aromatic ring and which may be bound (directly or via a linker) or bused with the hydroxy-substituted ring. This cyclic or heterocyclic ring may optionally be substituted with any substituent described in (a) above. This additional ring structure, alone or in combination with the hydroxy-substituted A-ring, may be selected from, for example, one or more of the following structures: phenanthrene; naphthalene; napthols; diphenyl; benzene; cyclohexane; 1,2-pyran; 1,4-pyran; 1,2-pyrone; 1,4-pyrone; 1,2-dioxin; 1,3-dioxin (dihydro form); pyridine; pyridazine; pyrimidine; pyrazine; piperazine; s-triazine; as-triazine; v-triazine; 1,2,4-oxazine; 1,3,2-oxazine; 1,3,6-oxazine (pentoxazole); 1,2,6-oxazine; 1,4-oxazine; o-isoxazine; p-isoxazine; 1,2,5-oxathiazine; 1,2,6-oxathiazine; 1,4,2-oxadiazine; 1,3,5,2-oxadiazine; and morpholine (tetrahydro-p-isoxazine). Additionally, any of the above carbon ring structures may be linked directly or via a linkage group to a heterocyclic aromatic or nonaromatic carbon ring, such as: furan; thiophene (thiofuran); pyrrole (azole); isopyrrole (isoazole); 3-isopyrrole (isoazole); pyrazole (1,2-daizole); 2-isoimidazole (1,3-isodiazole); 1,2,3-triazole; 1,2,4-triazole; 1,2-diothiole; 1,2,3-oxathiole, isoxazole (furo(a) monozole); oxazole (furo(b) monazole); thiazole; isothiazole; 1,2,3-oxadiazole; 1,2,4-oxadiazole; 1,2,5-oxadiazole; 1,3,5-oxadiazole; 1,2,3,4-oxatriazole; 1,2,3,5-oxatriazole; 1,2,3-dioxazole; 1,2,4-dioxazole; 1,3,2-dioxazole; 1,3,4-dioxazole; 1,2,5-oxathiazole; 1,3-oxathiole; and, cyclopentane. These compounds in turn may have associated substituent groups selected from section (a) or section (b), that are substituted on the ring at any of the available sites.

In this regard it is to be further noted that, in some embodiments, $R^z$ may be a cycloalkyl or cycloalkenyl (e.g., cyclopentyl, cyclopentenyl), or alternatively alkoxyl (wherein an ether substituent is present on, for example, the D-ring of the structure, including for example C1 to C8 alkoxy substituents, such as methoxy, ethoxy, propoxy, butoxy, pentoxy, etc.) or alkyloxy (wherein an ester substituent is present thereon). Additionally, $R^z$ may be a spiro structure, wherein a carbon of the ring to which it is attached is also a carbon of the cyclic structure. In a preferred embodiment t is 2 (i.e., 2 $R^z$ substituents are present), $R^z$ being a hydroxy or oxo substituent in combination with a spiro (e.g., cyclopentyl) substituent.

The core hydroxy-substituted structure, X, of the present invention may be a cyclopentanophen(a)anthrene ring compound, for example selected from the group consisting of the hydroxy-substituted analogs of: 1,3,5(10),6,8-estrapentaene; 1,3,5(10),6,8,11-estrahexaene; 1,3,5(10),6,8,15-estrahexaene; 1,3,5(10),6-estratetraene; 1,3,5(10),7-estratetraene; 1,3,5(10),8-estratetraene; 1,3,5(10),16-estratetraene; 1,3,5(10),15-estratetraene; 1,3,5(10)-estratriene; and 1,3,5(10),9(11)-estratetraene.

The present invention is further directed to any compound as described herein, as well as to the administration thereof to treat a cytodegenerative disease, including precursors or derivatives selected from raloxifen, tamoxifen, androgenic compounds, as well as their salts, where an intact hydroxy-bearing aromatic ring is present, with a hydroxy group present on carbons 1, 2, 3 and 4 of the terminal phenol ring.

These compounds may be in the form of a prodrug, which may be metabolized to form an active polycyclic phenolic, or catecholic, compound having cytoprotective, and in some cases neuroprotective, activity.

With respect to additional substituents (e.g., $R^2$, $R^3$, $R^4$, $R^5$, $R^x$, $R^y$, $R^v$, $R^z$, etc.), it is to be noted that when such additional substituents are present on the terminal, hydroxy-substituted aromatic ring, or proximate thereto, in some embodiments it is preferred that these substituents be small (e.g., methyl, ethyl, propyl, butyl), relative to the size of the $R^1$ substituent of the present invention. Stated another way, it is preferred that in some embodiments of the present invention only one large, hydrophobic group be attached to the hydroxy-bearing aromatic ring, or proximate thereto.

Additionally, it is to be noted that when a smaller substituent is present, it is preferred that this substituent likewise be hydrophobic in nature. Again, without being held to a particular theory, it is generally believed that the presence of a hydrophilic group may interfere with the position and/or orientation of the overall compound within the cell membrane or lipid bilayer.

Finally, it is to be noted that substituent $R^1$ may itself be substituted. For example, when $R^1$ is a non-fused polycyclic substituent, such as adamantyl, the adamantyl ring may optionally be substituted to increase the hydrophobicity (such as by attaching a halogen).

Additional Preferred Embodiments

1. Modification of the Hydroxy-substituted Aromatic Ring Structure

As previously noted, the core or terminal hydroxy-substituted aromatic ring structure may optionally be modified with one or more substituents in addition to the $R^1$ substituent (e.g., the non-fused polycyclic, hydrophobic substituent). In one preferred embodiment, the hydroxy-substituted aromatic ring is additionally modified with a substituted or unsubstituted hydrocarbyl (e.g., methyl, ethyl, propyl, butyl, etc.) substituent. More preferably, when $R^1$ is a non-fused polycyclic, hydrophobic substituent, such as adamantyl, the hydroxy-substituted aromatic ring is additionally modified with an alkyl substituent (such as methyl, ethyl, propyl, methylpropyl, etc.) or an alkenyl substituent (such as ethylene, propylene, methylpropylene, etc.). Even more preferably, these substituents are alpha or adjacent to the hydroxy group on the aromatic ring; that is, preferably the hydroxy group is between the two substituents, the two substituents occupying carbon atoms which are directly bound to the carbon atom occupied by the hydroxy group.

Additionally, it is to be noted that Applicant's experience to-date indicates that, in an alternative embodiment, a non-polycyclic, hydrophobic substituent (e.g., an alkyl or alkenyl substituent) may be employed to increase cytoprotective activity, relative to the non-substituted analog thereof. More specifically, experience to-date indicates that, in some embodiments, the hydroxy-substituted aromatic ring structure may be modified by the attachment of one or more groups selected from, for example, methyl, ethyl, propyl (e.g., n-propyl, isopropyl), propenyl, methylpropyl, methylpropenyl, butyl (e.g., isobutyl, t-butyl). In a preferred embodiment, a large or bulky alkyl group is employed, such as a t-butyl or a methyl-propyl group (or larger). In another preferred embodiment, the hydroxy-substituted ring may be modified with two such substituents, such as t-butyl/methyl or ethyl, propyl or propenyl/methyl or ethyl, etc.

2. Polycyclic, Hydroxy-substituted Aromatic Ring Structure

As previously noted, the core hydroxy-substituted aromatic ring structure may be part of a larger, polycyclic core structure (e.g., bicyclic, tricyclic, tetracyclic, etc.). In one preferred embodiment, the hydroxy-substituted core structure has the formula (VI):

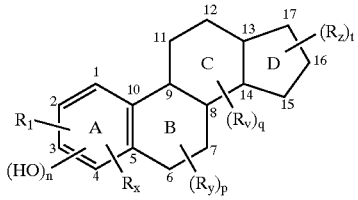

(VI)

wherein n is typically 1 or 2, $R^1$ is a large or bulky hydrophobic substituent (e.g., a non-fused polycyclic), the hydroxy-substituted ring being the terminal or A-ring of the structure, and $R^x$, $R^y$, $R^v$ and $R^z$ are as defined herein. More preferably, however, the compound of the present invention has the formula (VII):

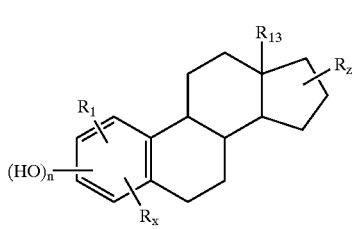

(VII)

wherein: n is as defined above, $R^1$ is a non-fused polycyclic, hydrophobic substituent (or alternatively a bulky hydrocarbyl group, such as t-butyl, methylpropyl, etc.); $R^x$ is selected from the group consisting of hydrogen and substituted or unsubstituted hydrocarbyl (e.g., alkyl); $R^{13}$ is hydrogen or substituted or unsubstituted hydrocarbyl (e.g., alkyl); and, $R^z$ is one or more substituents selected from hydrogen, hydroxy, substituted or unsubstituted alkyl, or oxo ($R^y$, $R^v$ being hydrogen). Some of the preferred combinations of such substituents include:

| $R^1$ | $R^x$ | $R^z$ |
|---|---|---|
| adamantyl | methyl | oxo |
| adamantyl | methylpropyl | hydroxy |
| t-butyl | hydrogen | hydroxy |
| adamantyl | hydrogen | hydroxy |
| methylpropyl | hydrogen | hydroxy |
| adamantyl | hydrogen | oxo |
| methylpropenyl | hydrogen | hydroxy |
| t-butyl | hydrogen | oxo |
| methylpropyl | hydrogen | oxo |
| t-butyl | methyl | oxo |
| hydrogen | methyl | oxo |
| methylpropenyl | hydrogen | oxo |
| hydrogen | methylpropenyl | oxo | wherein for example $R^1$, $R^x$ and $R^z$ occupy the C-2, C-4 and C-17 positions on the ring, respectively ($R^z$ being in the alpha or beta position when is it hydroxy, for example).

In this regard it is to be noted that the present invention encompasses a number of compounds having one or more chiral centers therein. Generally speaking, therefore, it is to be understood that the configuration at one or more of these chiral centers may change without departing from the scope of the intended invention; that is, it is to be understood that the present invention extend to compounds specifically or generally described herein, as well as all related diastereomers and enantiomers (e.g., (i) the naturally-occurring estrogen configuration wherein, when present, substituents at the C-8, C-9, C-13 and C-14 position are beta, alpha, beta and alpha, respectively, or (ii) the non-naturally-occurring estrogen configuration wherein, when present, these substituents have the alpha, beta, alpha, beta configuration).

Administration/Application

Generally speaking, the process of the present invention involves the treatment of a population of cells in a subject (e.g., animal or human), in order to confer cytoprotection to that population, by the administration of an effective dose of the above-described compound. Experience to-date suggests such protection can be achieved at low plasma concentrations, concentrations which can be significantly lower than those needed for the non-substituted (i.e., non-$R^1$ substituted) analogs of the present compounds. More specifically, a cytoprotective or even a neuroprotective effect can be achieved, in some cases, at plasma concentrations of less than about 10 µM, 1 µM, 500 nM, 100 nM, 10 nM, or even 1 nM (i.e., from about 0.1 nM to about 1 nM).

Administration of any of the compounds of the invention may be achieved by means standard in the art, and may include the use of a single compound or a mixture of cytoprotective compounds, their enantiomers or diastereomers, or pharmaceutically acceptable salts thereof. The recommended route of administration of the compounds of the present invention includes oral, intramuscular, transdermal, buccal, nasal, intravenous and subcutaneous. Methods of administering the compounds of the invention may be by dose or by controlled release vehicles.

Additionally, it is to be noted that, similar to the approach described by Simpkins et al. in U.S. Pat. No. 5,972,923 (incorporated herein by reference), a pharmaceutical preparation may also include, in addition to one or more compounds of the present invention, an additional antioxidant. As noted by Simpkins et al., in reference to compounds similar to those of the present invention, synergistic effects may be achieved in certain circumstances when such a combination is employed. For example, Simpkins et al. reports that estratrienes exhibit approximately a 1000–5000 fold enhancement in their cytoprotective effect when administered with the antioxidant, glutathione.

The present compounds are suitable, for example, in treating subjects suffering from trauma, chronic degenerative diseases or acute disease such as induced by an ischemic attack. Specific examples include Alzheimer's disease, Parkinson's disease, stroke, ischemia, heart attack or angioplasty, or brain or spinal cord trauma, hypoglycemia, anoxia, burns or surgeries that result in the loss of nutrient flow to the tissues. Other diseases that may be treatable with compounds of the current invention include: heart disease, including myocardial infarction, ophthalmologic diseases including macular degeneration, lens or retinal degeneration, formation of cataracts and glaucoma, alcoholism, alcohol withdrawal, drug-induced seizures vascular occlusion, epilepsy, cerebral vascular hemorrhage, hemorrhage; environmental excitotoxins, dementias of all type, drug-induced brain damage and other systemic or acute degenerative diseases characterized by necrotic or apoptotic cell death. To-date, there are no known cures and few therapies that slow the progression of these diseases. However, the present invention provides compounds which can be used as therapeutics or as prophylactics to treat, prevent or delay the onset of symptoms.

Certain embodiments of the present invention may further be applied to the procedure of tissue transplantation, prior, during or after removal or reperfusion of cells, tissues or organs or during storage of the cells, tissues or organs and is applicable to any of the cells in the body.

Preparation

Generally speaking, the compounds of the present invention may be prepared by means standard in the art. Specific details for the preparation of certain preferred compounds are provided herein in the Examples, below.

Activity

The activity of the compounds of the present invention may be determined by means standard in the art (see, e.g., U.S. Pat. Nos. 5,972,923; 5,877,169; 5,859,001; 5,843,934; 5,824,672; and, 5,554,601; all of which are incorporated herein by reference). Alternative methods for determining activity are described in detail herein in the Examples, below.

Definitions

As used herein, the following phrases or terms shall have the noted meanings; however, it is to be understood that these definitions are intended to supplement and illustrate, not preclude or replace, the definitions known to those of skill in the art.

"Hydroxy-substituted aromatic" or "hydyroxy-bearing aromatic" structure or ring, as well as variations thereof, refers to a terminal ring of a compound of the present invention which is both aromatic and substituted with one or more hydroxy groups. It is therefore to be understood that such phrases are intended to refer to compounds wherein the entire structure is aromatic (e.g., naphthalene, anthracene, and phenanthracene), as well as to compounds wherein only the terminal ring is aromatic (e.g., indan and 1,2,3,4-tetrahydronaphthlene).

"Cytoprotection" refers to the protection of cells against cell death or cell damage that would otherwise occur in the absence of a protective agent, where the cell death or cell damage might be caused by any mechanical damage, nutritional deprivation (including oxygen deprivation), trauma, disease processes, damage due to exposure to chemicals or temperature extremes, aging or other causes.

"Neuroprotection" is one form of cytoprotection and refers to the inhibition of the progressive deterioration of neurons that lead to cell death.

"Enhanced" cytoprotective or neuroprotective activity refers to the increase in activity of the compounds of the present invention (i.e., compounds having a large, hydrophobic substituent, $R^1$, attached), as compared to the non-substituted (i.e., non-$R^1$ substituted) analogs thereof.

"Non-fused, polycyclic" refers to polycyclic systems other than fused systems, and is intended to encompass bridged and spiro systems, as well as ring assemblies. (See, e.g., Naming and Indexing of Chemical Substances for Chemical Abstracts, a reprint of Appendix IV from the Chemical Abstracts 1997 Index Guide, ¶¶147–155, pp. 260I–266I.)

"Fused systems" are polycyclic structures containing at least two rings of five or more members having (i) only "ortho" fusion, wherein adjoining rings have only two atoms in common and thus have n common faces and 2n common atoms, such as naphthalene, or (ii) "ortho" and "peri" fusion, wherein a ring has two, and only two, atoms in common with each of two or more rings, the total system containing n common faces and fewer than 2n common atoms, such as pyrene. (See, e.g., Id.)

"Bridged systems" are monocyclic or fused systems with valence bonds, atoms or chains connecting different parts of the structure.

"Spiro systems" have pairs of rings (or ring systems) with only one common atom. (See, e.g., Id.)

"Ring assemblies" have pairs of rings (or ring systems) connected by single bonds. (See, e.g., Id.)

An "estrogen compound" refers to any of the structures described in the 11th Edition of "Steroids" from Steraloids Inc., Wilton N. H., incorporated herein by reference. Included in this definition are isomers and enantiomers, including non-steroidal estrogens formed by modification or substitution of the compounds in the Steraloid reference. Other estrogen compounds included in this definition are estrogen derivatives, estrogen metabolites and estrogen precursors, as well as those molecules capable of binding cell-associated estrogen receptors as well as other molecules where the result of binding specifically triggers a characterized estrogen effect. Also included are mixtures of more than one estrogen, where examples of such mixtures are provided in, for example, U.S. Pat. No. 5,972,923. Examples of α-estrogen structures having utility either alone or in combination with other agents are provided in, for example, U.S. Pat. No. 5,972,923 as well.

A "non-estrogen compound" refers to a compound other than an estrogen compound as defined above.

The terms "17-E2," "β-estradiol," "17β-estradiol," "β-17-E2," "17β-E2," "E2," "17βE2," and "βE2," are intended to be synonymous. Similarly, the terms "α17-E2," "α-17-E2," "α-estradiol," "17α-estradiol," "17αE2," and "αE2," as defined here and in the claims, are intended to be synonymous and correspond to the α-isomer of 17β-estradiol.

"E-3-ol" refers to estra-1,3,5(10)-trien-3-ol.

The terms "polycyclic phenolic compound," "polycyclic compounds" or "polycyclic phenols" as used herein are generally synonymous and are defined, for example, in U.S. Pat. No. 5,859,001 (herein incorporated by reference); the terms generally include any compound having a phenolic A ring and may contain 2, 3, 4 or even more additional ring structures exemplified by the compounds described herein.

A "steroid" refers to a compound having numbered carbon atoms arranged in a 4-ring structure (see, e.g., J. American Chemical Society, 82:5525–5581 (1960); and, Pure and Applied Chemistry, 31:285–322 (1972)).

A "cytodegenerative" disorder or disease refers to a disorder or disease related to cell death or cell damage, which might be caused by any mechanical damage, nutritional deprivation (including oxygen deprivation), trauma, disease processes, damage due to exposure to chemicals or temperature extremes, aging or other causes.

A "neurodegenerative disorder" or "neurodegenerative disease" refers to a disorder or disease in which progressive loss of neurons occurs either in the peripheral nervous system or in the central nervous system. Examples of neurodegenerative disorders include: chronic neurodegenerative diseases, such as Alzheimer's disease, Parkinson's disease, Huntington's chorea, diabetic peripheral neuropathy, multiple sclerosis, amyotrophic lateral sclerosis; aging; and acute neurodegenerative disorders including: stroke, traumatic brain injury, schizophrenia, peripheral nerve damage, hypoglycemia, spinal cord injury, epilepsy, and anoxia and hypoxia.

"Linker" embraces a saturated or partially unsaturated moiety, typically a hydrocarbylene (e.g., alkylene, akenylene, akynylene), or alternatively a hetero-substituted hydrocarbylene (e.g., wherein a carbon in the main chain has been substituted by a heteroatom, such as oxygen or sulfur), interposed between the core ring structure X and the modifying hydrophobic substituent, $R^1$, or alternatively between the core ring structure X and another substituent (e.g., $R^2$, $R^3$, etc.).

"Hydrocarbyl" embrace moieties consisting exclusively of the elements carbon and hydrogen, in a straight or branched chain, or alternatively a cyclic structure, which may optionally be substituted with other hydrocarbon, halo (e.g., chlorine, fluorine, bromine) or hetero (e.g., oxygen, sulfur) substituents. These moieties include alkyl, alkenyl, alkynyl and aryl moieties, as well as alkyl, alkenyl, alkynyl and aryl moieties substituted with other aliphatic or cyclic hydrocarbon groups such as, for example, alkaryl, alkenaryl and alkynaryl.

The alkyl groups described herein are, in some embodiments, preferably lower alkyl containing from about 1 to about 6 carbon atoms in the principal chain. They may be straight or branched chains and include methyl, ethyl, propyl, isopropyl, butyl, isobutyl, tertiary butyl, pentyl, hexyl and the like. They may be substituted with aliphatic or cyclic hydrocarbon moieties or hetero-substituted with the various substituents defined herein.

The alkenyl groups described herein are, in some embodiments, preferably lower alkenyl containing from about 2 to about 6 carbon atoms in the principal chain. They may be straight or branched chains and include ethenyl, propenyl, isopropenyl, butenyl, isobutenyl, pentenyl, hexenyl, and the like. They may be substituted with aliphatic or cyclic hydrocarbon moieties or hetero-substituted with the various substituents defined herein.

The alkynyl groups described herein are, in some embodiments, preferably lower alkynyl containing from about 2 to about 6 carbon atoms in the principal chain. They may be straight or branched chain and include ethynyl, propynyl, butynyl, isobutynyl, pentynyl, hexynyl, and the like. They may be substituted with aliphatic or cyclic hydrocarbon moieties or hetero-substituted with the various substituents defined herein.

The term "cycloalkyl" is used herein to refer to a saturated cyclic non-aromatic hydrocarbon moiety having a single ring or multiple condensed rings. Exemplary cycloalkyl moieties include, for example, cyclopentyl, cyclohexyl, cyclooctanyl, etc.

The term "cycloalkenyl" is used herein to refer to a partially unsaturated (i.e., having at least one carbon-carbon double bond), cyclic non-aromatic hydrocarbon moiety having a single ring or multiple condensed rings. Exemplary cycloalkenyl moieties include, for example, cyclopentenyl, cyclohexenyl, cyclooctenyl, etc.

"Substituted cycloalkyl" and "substituted cycloalkenyl" refer to cycloalkyl and cycloalkenyl moieties, respectively, as just described wherein one or more hydrogen atoms to any carbon of these moieties is replaced by another group such as a halogen, alkyl, alkenyl, alkynyl, substituted alkyl, substituted alkenyl, substituted alkynyl, aryl, substituted aryl, cycloalkyl, cycloalkenyl, substituted cycloalkyl, substituted cycloalkenyl, heterocyclo, substituted heterocyclo, heteroaryl, substituted heteroaryl, alkoxy, aryloxy, boryl, phosphino, amino, silyl, thio, seleno and combinations thereof.

"Hydrophobic," as used in the context of the substituent attached to the hydroxy-substituted aromatic ring structure (i.e., R1), generally refers to this substituent's affinity for nonaqueous environments, and more specifically to its affinity for the hydrophobic region of a lipid bilayer upon introduction thereto.

"Terminal," as used in the context of the hydroxy-substituted aromatic ring structure, generally refers to the position of the ring relative to the rest of the molecule, the ring being located at or proximate one end of the molecule, such as in the case of the tetracyclic estrogen compounds (the hydroxy-substituted aromatic ring being the A ring of the compound).

The following Examples set forth one approach for preparing and testing compounds in accordance with the present invention. These Examples are intended to be illustrative of compounds preferred for certain embodiments only, as well as their respective activity in the protection of neuron. Generally speaking, however, it is understood that in many cases drugs which protect neurons are also active in protecting non-neuronal cells. Accordingly, in advancing the understanding of the structural requirements for compositions capable of inducing neuroprotection, these results in turn provide the basis for designing novel drugs that have enhanced cytoprotective properties, as well. Therefore, these Examples should not be viewed in a limiting sense.

EXAMPLE 1

Preparation of 2-(1-Adamantyl)-3-hydroxyestra-1,3,5(10)-trien-17-one

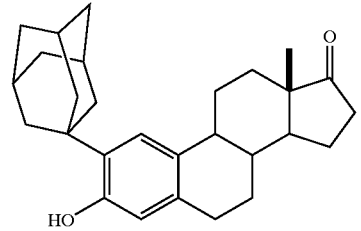

Estrone [3-hydroxyestra-1,3,5(10)-trien-17-one, 270 mg, 1 mmol) and 1-adamantanol (170 mg, 1 mmol) were added to anhydrous n-pentane (6 mL) and the stirred mixture was cooled with an ice bath. Boron trifluoride etherate ($BF_3$.EtOEt, 0.4 mL) was added over a 10 minute period. After an additional 15 minutes, the ice bath was removed and stirring was continued for an additional 45 minutes at room temperature. During the 45 minute period, solids present in the reaction mixture were dissolved and a yellow oil formed. Crushed ice was then added while shaking and swirling the reaction flask and a pink solid was formed. The filtered, crude pink product was washed with water until the filtrate had a neutral pH, and then the solid was dried in a vacuum oven at 50° C. The crude pink powder (0.4 g) was purified by flash chromatography (silica gel eluted with 20% ethyl acetate in hexanes) to get the pure product (0.31 g, 76.7%). The product was recrystallized from a mixture of chloroform and isopropyl alcohol and characterized as follows: (i) melting point=322–324° C. (see, e.g., Lunn, W. H. W.; Farkas, E., Adamantyl Carbonium Ion as a Dehydrogenating Agent: Its Reactions with Estrone, Tetrahedron 1969, 24, 6773-76, citing melting point as 295–296° C.); (ii) $^1$H NMR ($CDCl_3$, 300 MHZ) δ0.94 (s, 3H, $C_{18}$—$CH_3$), 2.8 (m, 2H, $C_6$—$CH_2$) 4.7 (s, 1H, $C_3$—OH), 6.4 (s, 1H, $C_4$—H), 7.12 (s, 1H, $C_1$—H); (iii) $^{13}$C NMR ($CDCl_3$, 300 MHZ) δ13.76, 21.47, 25.93, 26.41, 28.63, 28.95 (3×C), 31.56, 35.81, 36.56, 36.98 (3×C), 38.42, 40.69 (3×C), 44.25, 47.99, 50.35, 116.87, 124.11, 131.59, 134.00, 135.02, 152.44, 221.43. (Chemical Abstracts Registry Number [21003-01-0].)

EXAMPLE 2

Preparation of (17β)-2-(1-Adamantyl)-estra-1,3,5(10)-triene-3,17-diol

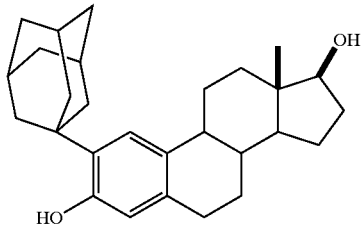

2-(1-Adamantyl)-3-hydroxyestra-1,3,5(10)-trien-17-one (250 mg, 0.62 mmol) was added to cold ethanol (25 mL) and methanol (10 mL) to give a turbid solution. Sodium borohydride (NaBH$_4$, 140 mg) was added in one portion and the reaction was continued with stirring for 2 hours. Solvents were removed on a rotary evaporator and crushed ice was added. On standing overnight, the initially formed oil became a solid. The solid was filtered and washed with water until the filtrate was pH neutral. The solid was dried in a vacuum oven at 50° C. to give the crude product (0.25 g), which was purified by flash chromatography (silica gel eluted with 18% ethyl acetate in hexanes). The pure product (200 mg, 79.6%) was recrystallized from chloroform and hexanes to obtain crystals (150 mg), and was then characterized as follows: (i) melting point=174–175° C.; (ii) $^1$H NMR (CDCl$_3$, 300 MHZ) δ0.81 (s, 3H, C$_{18}$—CH$_3$), 2.76 (m, 2H, C$_6$—CH$_2$), 3.73 (t, 1H, C$_{17}$—H), 4.78 (s, 1H, C$_3$—OH), 6.38 (s, 1H, C$_4$—H), 7.16 (s, 1H, C$_1$—H); (iii) $^{13}$C NMR (CDCl$_3$, 300 MHZ) δ10.95, 23.02, 26.33, 27.12, 28.77, 28.98 (3×C), 30.49, 36.54, 36.71, 37.01 (3×C), 38.89, 40.68 (3×C), 43.20, 44.22, 49.96, 81.99, 116.84, 124.06, 132.06, 133.83, 135.20, 152.36.

EXAMPLE 3

Comparative Study of the Activity of 17-β-estradiol and Adamantyl-modified Analog Thereof Methods Glial cell cultures: Glial cell cultures were prepared from P1 mice. Briefly, cortex from P1 mice were dissected and digested with 0.025% trypsin for 30–40 min. After trituration, the cells were plated on poly-D-lysine/laminin coated glass-bottom dishes at a density of approximately 5×10$^6$ cells per dish. Cells were grown for 7–10 days in Eagle's minimal essential medium supplemented with 10% fetal bovine serum, 10% horse serum, 10 ng/ml epidermal growth factor, 2 mM glutamine and 20 mM glucose. Cultures were kept at 37° C. in a humidified CO$_2$ atmosphere until they reached confluence. Cultures were then used to support neurons (see below).

Cortical neuronal cultures: Cortical neurons were prepared from E15–16 mouse embryos. Dissociated cortical cells (at a density of 5×10$^6$ cells per dish) were plated on a layer of confluent glial cells (7–10 days in vitro), into Eagle's minimal essential medium supplemented with 5% fetal bovine serum, 5% horse serum, 2 mM glutamine, and 21 mM glucose. Cultures were kept at 37° C. in a humidified 5% CO$_2$ atmosphere. After 3–5 days in vitro, non-neuronal cell division was halted by exposure to 10$^{-5}$ M cytosine arabinoside for 2 days, and cultures were shifted to a growth medium identical to the plating medium but lacking 10% fetal bovine serum. Cultures 9–14 days in vitro were used for the experiments.

Neuronal cell death: Mixed neuron/glial cultures were exposure to NMDA (30 μM) for 24 hours in medium stock (MS) (minimal essential medium with 15.8 mM NaHCO$_3$ and 20 mM glucose, pH 7.4) at 37° C. Cell death was assessed qualitatively by counting cells that stained with Trypan blue (0.4% for 10 minutes at 37° C.). Stained neurons were counted from three random fields per dish. For the experiments to test the neuroprotective effect of the 17-β-estradiol and the adamantyl-modified analog thereof, cultures were incubated with the drugs for various time periods prior to when NMDA was added to the medium.

Results

Figure 5:
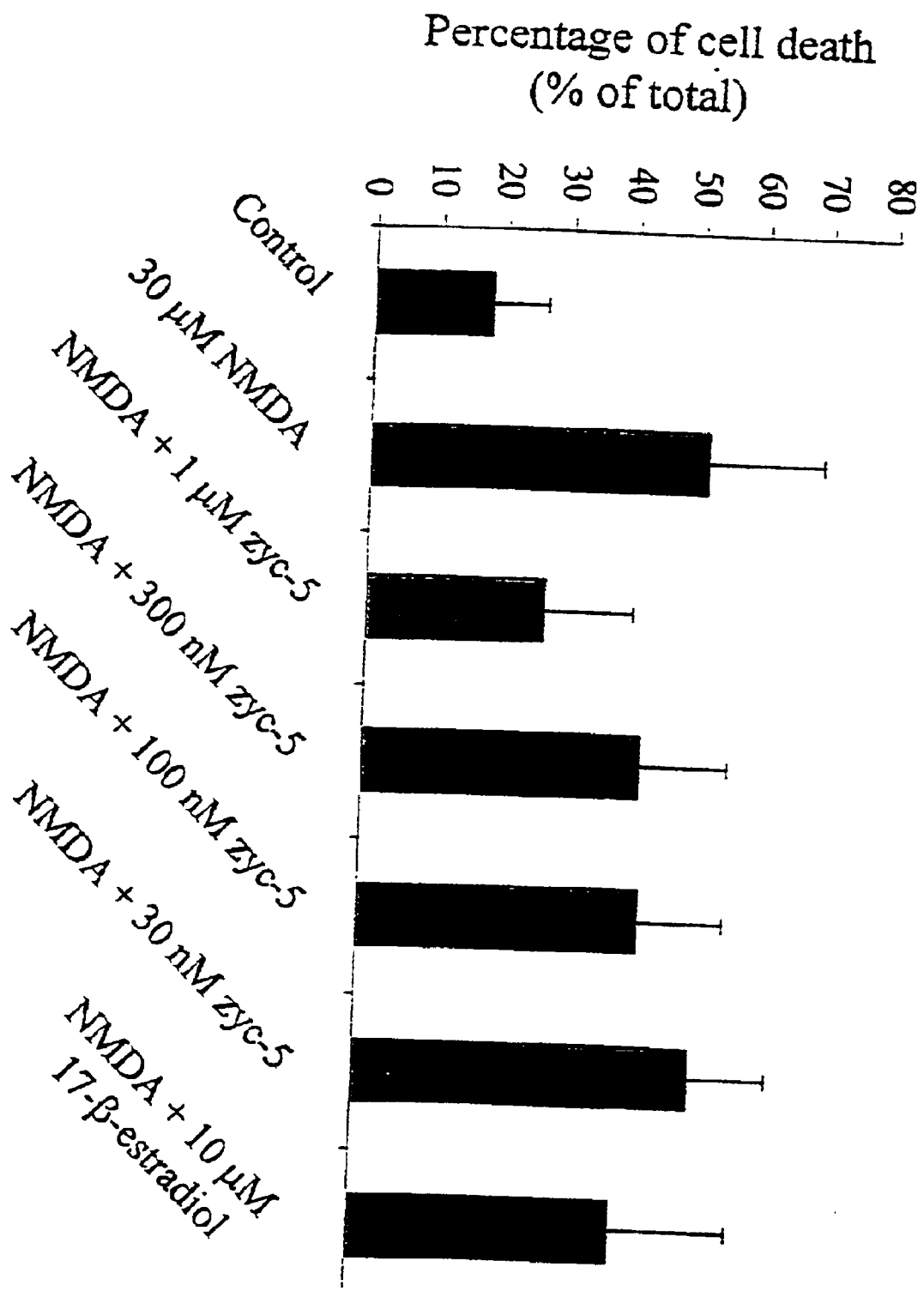
FIG. 5 is a bar graph which, as further described in Example 3 below, illustrates the results of analyses performed to examine the impact a compound of the present invention had on cell death, at varying dosages.

As seen by others, 24 hour pre-incubation with 17-β-estradiol attenuated cortical cell death induced by 24 hour exposure to 30 μM NMDA. We found that adamantyl-modified analog was more effective in protecting cortical neurons from excitotoxicity. As shown in FIG. 5, 10 μM 17-β-estradiol reduced neuronal loss due to NMDA exposure by about 15%, whereas 1 μM of the adamantyl-modified analog (denoted zyc-5) protected neuronal death by about half; that is, at one-tenth the dosage, the adamantyl-modified compound was found to be more than three times more effective. The protective effect of adamantyl-modified compound was dose-dependent, dropping to 10% with a 100 nM dosage.

Figure 6:
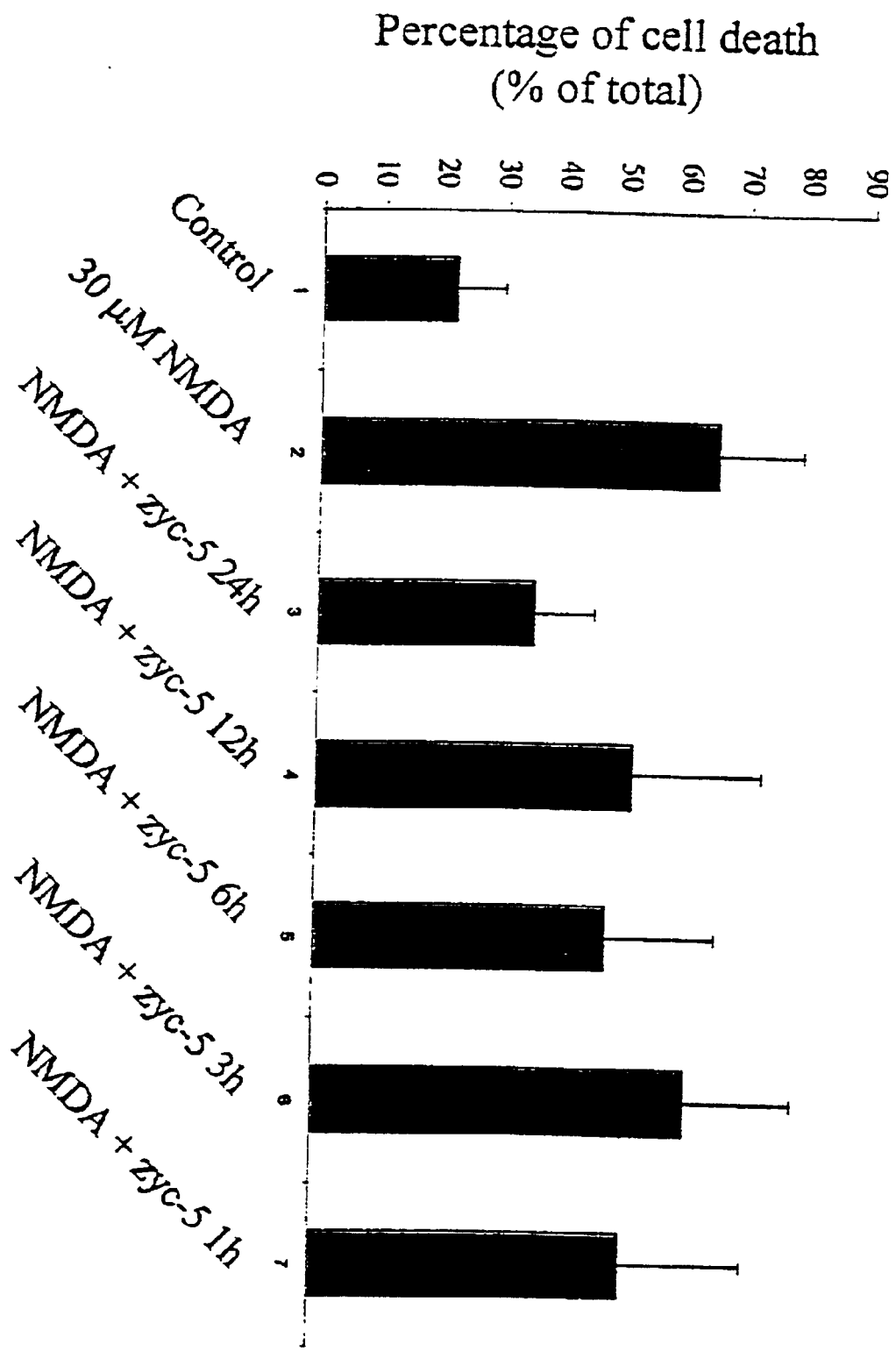
FIG. 6 is a bar graph which, as further described in Example 3 below, illustrates the results of analyses performed to examine the impact varying exposure times (to a compound of the present invention) had on cell death.

Referring now to FIG. 6, cultured cortical neurons were pre-incubated with 1 μM of the adamantyl-modified compound for 1, 3, 6, 12 and 24 hour(s) prior to NMDA exposure. There was no significant difference of neuronal survival from 1–12 hours pre-incubation; 24 hours pre-incubation gave the best protection results.

EXAMPLE 4

Preparation of 3-Hydroxy-2-(1methylpropyl)-estra-1,3,5(10)-trien-17-one

To a solution of the known 3-hydroxy-2-(1-methyl-2-propenyl)estra-1,3,5(10)-trien-17-one (ref. Patton, 1962; Chemical Abstracts Registry Number [98543-85-2], 30 mg, 0.093 mmol) dissolved in 10 mL of anhydrous ethanol was added 20 mg of 5% Pd/C. The reaction flask was shaken under 2.7 atm. of hydrogen for 3 h. The reaction mixture was then filtered and the catalyst was washed with ethanol. After solvent removal, the crude product was purified by chromatography (silica gel eluted with 12.5% ethyl acetate in hexanes) and then recrystallized from methylene chloride-hexanes to give 20 mg of pure product: m.p. 186–187° C.; $^1$H NMR(CDCl$_3$) δ 0.85–0.90 (m, 3H, CH$_3$), 0.91 (s, 3H, CH$_3$), 1.20–1.24 (m, 3H, CH$_3$), 2.81–2.89 (m, 2H, CH$_2$), 6.51 (s, 1H, Ar—H), 7.06 (s, 1H, Ar—H); $^{13}$C NMR(CDCl$_3$) δ 12.17, 13.75, 20.44, 21.46, 25.93, 28.91, 29.83, 31.49, 33.87, 35.81, 38.33, 44.05, 48.01, 50.24, 115.37, 123.99, 124.17, 130.86, 131.88, 134.78, 157.267, 221.79.

EXAMPLE 5

Preparation of 2-(1,1-Dimethylethyl)-3-hydroxy-4-methylestra-1,3,5(10)-trien-17-one To a suspension of the known 3-hydroxy-4-methylestra-1,3,5(10)-trien-17-one (ref. Kaneko et al., 1964; Chemical Abstracts Registry Number [68969-90-4], 30 mg, 0.11 mmol) in 1 mL of anhydrous pentane and 0.5 mL of t-butanol, was added 0.03 mL of boron trifluoride diethyl etherate while cooling with an ice bath and stirring. After 20 min., the reaction was stirred at room temperature for 2.5 h. Ice was added and the solid that formed was filtered, washed with water and dried overnight in a vacuum desiccator. The crude product was purified by chromatography (silica gel eluted with 10% ethyl acetate in hexanes) and then recrystallized from methylene chloride-hexanes to give 20 mg of pure product (56% yield): m.p.190–192° C.; $^1$H NMR (CDCl$_3$) δ 0.90 (s, 3H, CH$_3$), 1.42 (s, 9H, C(CH$_3$)$_3$) 2.13 (s, 3H, CH$_3$) 2.79–2.81 (m, 2H, CH$_2$), 7.16 (s, 1H, Ar—H); $^{13}$C NMR (CDCl$_3$) δ 11.06, 13.70, 21.44, 26.16, 26.60, 26.68, 27.54, 29.82 (3×C), 31.55, 34.43, 35.84, 37.63, 44.52, 47.89, 50.34, 121.42, 131.28, 133.00, 133.55, 150.56, 221.45. (Anal. calc'd. for C$_{23}$H$_{32}$O$_2$: C, 81.13; H, 81.09. Found: C, 81.09; H, 9.59.)

EXAMPLE 6

Preparation of 2-(1-admantanyl)-3-hydroxy-4-methylestra-1,3,5(10)-trien-17-one

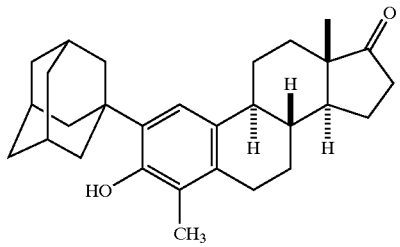

To a suspension of the known 3-hydroxy-4-methylestra-1,3,5(10)-trien-17-one (ref. Kaneko et al., 1964; Chemical Abstracts Registry Number [68969-90-4], 30 mg, 0.11 mmol) and 30 mg (0.197 mmol) of 1-adamantanol in 1 mL of anhydrous pentane was added 0.02 mL of boron trifluoride diethyl etherate while cooling with an ice bath and stirring. After stirring at 0° C. for 15 min. the reaction was stirred at room temperature for 45 min. Ice was added and the white solid that formed was filtered, washed with water and dried over P$_2$O$_5$. The crude product was purified by chromatography (silica gel eluted with 7% ethyl acetate in hexanes) to give 30 mg of pure product (68% yield). After recrystallization from methylene chloride-hexanes the product had: m.p. 262–263° C.; $^1$H NMR(CDCl$_3$) δ 0.90 (s, 3H, CH$_3$), 2.13 (s, 3H, CH$_3$), 2.7 (m, 2H, CH$_2$), 7.11 (s, 1H, Ar—H); $^{13}$C NMR (CDCl$_3$) δ 11.02, 13.70, 21.44, 26.22, 26.67, 27.54, 28.95 (3×C), 31.56, 35.84, 36.60, 36.98 (3×C), 37.63, 40.82 (3×C), 44.60, 47.91, 50.34, 121.41, 121.51, 131.45, 133.32, 150.79, 221.49. (Anal. calc'd. for C$_{29}$H$_{39}$O$_2$: C, 83.21; H, 9.15. Found: C, 83.45; H, 8.94.)

EXAMPLE 7

Preparation of (17β)-2-(1-Adamantyl)-4-(1-methylpropyl)estra-1,3,5(10)-triene-17-diol

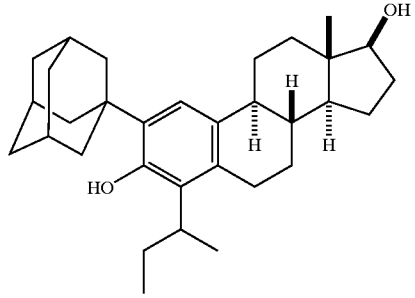

(A two step synthesis was involved, the first compound being an intermediate and the second being the above-referenced compound): To a mixture of the known 3-hydroxy-4-(1-methylpropyl)estra-1,3,5(10)-trien-17-one (ref. Miller et al., 1996; Chemical Abstracts Registry Number [177353-06-9], 70 mg, 0.215 mmol) and 50 mg (0.328 mmol) of 1-adamantanol in 2 mL of anhydrous pentane was added 0.1 mL of boron trifluoride diethyl etherate while cooling with an ice bath and stirring. After 1 h, stirring was continued at room temperature for an additional 1 h and a yellowish orange suspension formed. After adding ice, the reaction mixture was extracted with ethyl acetate. The combined extracts were washed with brine and dried over anhydrous sodium sulfate. After solvent removal, the crude product was purified by chromatography (silica gel eluted with 6% ethyl acetate in hexanes) to give 40 mg of product (40.5% yield) as a oil. $^1$H NMR(CDCl$_3$) δ 0.84–0.99 (m, 3H, CH$_3$), 0.90 (s, 3H, CH$_3$), 2.86–3.16 (m, 2H, CH$_2$); $^{13}$C NMR(CDCl$_3$) δ 13.05, 13.35, 13.67, 13.72, 13.97, 18.30, 21.43, 22.52, 26.22, 27.04, 27.45, 27.57, 28.29, 28.97 (3×C), 31.47, 31.62, 33.82, 34.23, 35.84, 36.68, 36.98 (3×C), 37.33, 37.40, 40.96 (3×C), 44.80, 47.85, 50.44, 122.01, 130.33, 132.92, 133.80, 152.49, 221.32.

To prepare the above-referenced compound, to a solution of 40 mg (0.087 mmol) of 2-(1-adamantyl)-3-hydroxy-4-(1-methylpropyl)estra-1,3,5(10)-trien-17-one in 5.5 mL of anhydrous methanol, at −10° C. was added 50 mg of sodium borohydride in one portion and the stirring was continued at −5° C. for 1 h. After solvent removal, ice was added and the solid that formed was filtered, washed with water and dried over P$_2$O$_5$. Purification by chromatography (silica gel eluted with 12.5% ethyl acetate in hexanes) gave 20 mg of purified product (50% yield) that had: m.p.152–154° C.; $^1$H NMR (CDCl$_3$) δ 0.78 (s, 3H, CH$_3$), 0.85–0.95 (overlapping t, J=7.4 Hz, 3H, CH$_3$), 1.34–1.36 (d, J=7.4 Hz, 3H, CH$_3$), 2.81–2.84 (m, 2H, CH$_2$) 3.74 (t, J=8.1 Hz, 1H, CHOH), 7.12 (m, 1H, Ar—H); $^{13}$C NMR(CDCl$_3$) δ 10.86, 10.90, 13.06, 13.37, 18.30, 22.97, 26.60, 27.69, 28.32, 29.00 (3×C), 30.58, 33.75, 34.17, 36.68, 36.78, 37.00 (3×C), 37.79, 37.86, 40.96 (3×C), 43.07, 44.78, 44.82, 50.08, 81.93, 121.98, 130.27, 131.89, 133.14, 133.67, 152.33.

EXAMPLE 8

Preparation of Ent-(17β)-2-(1-Adamantyl)estra-1,3,5(10)-triene-3,17-diol

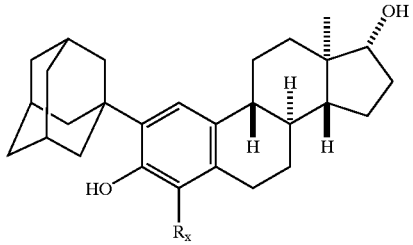

A suspension of the known ent-17β-estradiol (ref. Green et al., 2001, Chemical Abstracts Registry Number [3736-22-9], 40 mg, 0.147 mmol) and 20 mg of 1-adamantanol (0.13 mmol) in 1 mL anhydrous pentane was stirred at room temperature for 20 min. and then at −5° C. for 15 min. To this suspension was added 0.05 mL of boron trifluoride ditheyl etherate over 1 min. Then it was stirred at 0° C. to −5° C. for 20 min. and a pale yellow solution was obtained. The reaction then was stirred at room temperature for 15 min., during which time a sticky substance was formed. After 45 min., ice was added with stirring until the sticky substance solidified. The solid was then filtered, washed with water and dried in a vacuum desiccator to yield 50 mg of crude product. Purification by chromatography (silica gel eluted with 20% ethyl acetate in hexanes) gave 40 mg of pure product (67% yield). After crystallization from methylene chloride the pure product had: m.p.174–176° C.; [α] (24, D) –198 (c=0.1, CHCl$_3$); $^1$H NMR(CDCl$_3$) δ 0.78 (s, 3H, CH$_3$); 2.75–2.76 (m, 2H, CH$_2$); 3.78 (t, J=8Hz, 1H, CHOH); 6.39 (s, 1H, Ar—H); 7.15 (s, 1H, Ar—H); $^{13}$C NMR(CDCl$_3$) δ 152.16, 135.16, 133.73, 132.13, 124.02, 116.81, 81.98, 50.08, 44.31, 43.29, 40.82 (3×C), 39.01, 37.10 (3×C), 36.81, 36.64, 30.65, 29.10 (3×C), 28.87, 27.22, 26.44, 23.14, 11.07. (Anal. calc'd. for C$_{28}$H$_{38}$O$_2$: MS m/z 406(M$^+$).)

EXAMPLE 9

Preparation of Ent-(17β)-2-(1,1-dimethylethyl)estra-1,3,5(10)-triene-3,17-diol

A suspension of the known ent-17β-estradiol (ref. Green et al., 2001, Chemical Abstracts Registry Number [3736-22-9], 30 mg, 0.11 mmol) and 0.06 mL of 2-methyl-2-propanol (0.63 mmol) in 1 mL anhydrous pentane was stirred at room temperature 15 min. and then at 0° C. to –5° C. for 20 min. To this suspension was added 0.07 mL boron trifluoride diethyl etherate over 1 min. and stirring was continued at 0° C. to –5° C. for 20 min. The reaction was allowed to warm to room temperature and during this period (~15 min.) a yellow solid that stuck to the flask was formed. After stirring for 30 min. at room temperature, ice was added. The powder-like solid was filtered, washed with water and dried in a vacuum desiccator over night. The crude product was purified by chromatography (silica gel eluted with 18% ethyl acetate in hexanes) to get the pure product which was then crystallized from acetone-hexane. The pure product (20 mg, 55% yield) had: m.p.177–179° C.; [α] (25, D) –91.33 (c=0.225, CHCl$_3$); $^1$H NMR(CDCl$_3$) δ 0.78 (s, 3H, CH$_3$), 1.40 (s, 9H, C(CH$_3$)$_3$), 2.74–2.75 (m, 2H, CH$_2$), 3.74 (t, J=8.4 Hz, CHOH), 6.41 (s, 1H, Ar—H); 7.19 (s, 1H, Ar—H); $^{13}$C NMR(CDCl3) δ 152.05, 135.33, 133.37, 131.81, 124.04, 116.55, 81.98, 60.44, 50.03, 44.23, 43.26, 38.98, 36.78, 34.47, 30.57, 29.74 (3×C), 28.90, 27.22, 26.38, 23.12, 14.17, 11.07. (Anal. calc'd. for C$_{22}$H$_{32}$O$_2$: MS m/z 328 (M$^+$), 313.)

EXAMPLE 10

Comparative Study of Compound Activity

Method: HT-22 Cell Neuroprotection Assay

HT-22 cells (immortalized hippocampal neurons of murine origin) were maintained in DMEM media (Life Technologies, Inc., Gaithersburg, Md.) supplemented with 10% charcoal-stripped FBS (HyClone Laboratories, Inc., Logan, Utah) and 20 μg/mL gentamycin, according to standard culture conditions.

Cells were plated at a density of 5,000 cells/well in clear-bottomed Nunc 96-well plates (Fisher Scientific, Orlando, Fla.) and allowed to incubate overnight. Steroids dissolved in DMSO were added at concentrations ranging from 0.01–10 μM and were co-administered with glutamate (10 mM or 20 mM). DMSO was used at concentrations of 0.1% vol/vol as a vehicle control and had no discernible effect on cell viability. After ~16 h of glutamate exposure, cells were rinsed with PBS, pH 7.4, and viability was assessed by the addition of 25 μM calcein AM (Molecular Probes, Inc., Eugene, Oreg.) in PBS for 15 min at room temperature. Fluorescence was determined (excitation 485, emission 530) using a fluorescence FL600 microplate reader (Biotek, Winooski, Vt.). Cells that were lysed by addition of methanol were used for blank readings. All data were normalized to % cell death, as calculated by (control value–insult value)/control value×100.

Results

Test results are presented in Tables 1 and 2, below.

TABLE 1

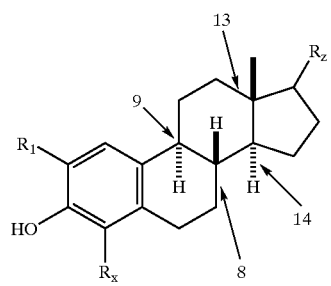

| Compound | $R_1$ | $R_x$ | $R_z$ | Steroid concentration needed to protect 50% of neurons killed by 10 mM Glutamate ED$_{50}$ (μM) | Steroid concentration needed to protect 50% of neurons killed by 20 mM Glutamate ED$_{50}$ (μM) |
|---|---|---|---|---|---|
| 1 ZYC-26 | Adamantyl | Me | =O | 0.018 | 0.030 |
| 2 ZYC-22 | Adamantyl | sec-Butyl | β-OH | 0.021 | 0.022 |
| 3 ZYC-15 | t-Butyl | H | β-OH | 0.045 | 0.14 |
| 4 ZYC-21 | sec-Butyl | H | β-OH | 0.16 | 0.29 |
| 5 ZYC-3 | Adamantyl | H | =O | 0.17 | 0.38 |
| 6 ZYC-20 | sec-But-2-enyl | H | β-OH | 0.24 | 0.31 |
| 7 ZYC-14 | t-Butyl | H | =O | 0.25 | 0.30 |
| 8 ZYC-19 | sec-Butyl | H | =O | 0.29 | 0.32 |
| 9 ZYC-25 | t-Butyl | Me | =O | 0.32 | 0.32 |
| 10 ZYC-5 | Adamantyl | H | β-OH | 0.39 | 0.16 |
| 11 ZYC-17 | H | sec-Butyl | =O | Not Done | 0.33 |
| 12 ZYC-24 | Me | H | =O | 0.51 | 0.52 |
| 13 ZYC-18 | sec-But-2-enyl | H | =O | 0.52 | 0.90 |
| 14 ZYC-16 | H | sec-But-2-enyl | =O | 0.66 | 0.70 |

TABLE 1-continued

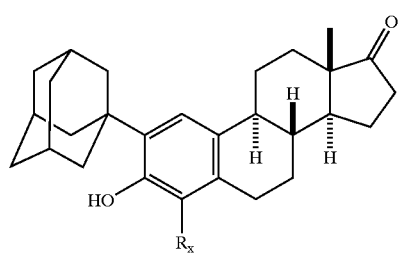

| Compound | $R_1$ | $R_x$ | $R_z$ | Steroid concentration needed to protect 50% of neurons killed by 10 mM Glutamate $ED_{50}$ ($\mu$M) | Steroid concentration needed to protect 50% of neurons killed by 20 mM Glutamate $ED_{50}$ ($\mu$M) |
|---|---|---|---|---|---|
| 15 17β-Estradiol | H | H | β-OH | 2.21 | 3.01 |
| 16 Estrone | H | H | =O | 3.03 | Not Done |
| 17 17α-Estradiol | H | H | α-OH | 3.10 | 16.12 |

TABLE 2

| Compound | $R_1$ | $R_x$ | $R_z$ | Steroid concentration needed to protect 50% of neurons killed by 10 mM Glutamate $ED_{50}$ ($\mu$M) | Steroid concentration needed to protect 50% of neurons killed by 20 mM Glutamate $ED_{50}$ ($\mu$M) |
|---|---|---|---|---|---|
| 1 ZYC-33 | Adamantyl | H | α-OH | 0.065 | 0.019 |
| 2 ZYC-34 | t-Butyl | H | α-OH | 0.24 | 0.26 |
| 3 Ent-(17β)-Estradiol | H | H | α-OH | 1.07 | 1.27 |

In view of the above, it will be seen that the several objects of the invention are achieved. As various changes could be made in the above process and compound without departing from the scope of the invention, it is intended that all matter contained in the above description be interpreted as illustrative and not in a limiting sense.

What is claimed is:

1. A compound having the formula:

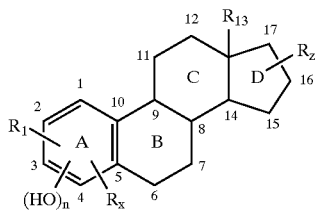

wherein: n is 1 or 2; $R^1$ is a non-fused polycyclic, hydrophobic substituent having a bridged structure; $R^x$ is selected from the group consisting of hydrogen and substituted or unsubstituted alkyl; $R^{13}$ is hydrogen or substituted or unsubstituted alkyl; and, $R^z$ is hydrogen, hydroxy, substituted or unsubstituted alkyl, or oxo, with the proviso that when the compound has the following structure:

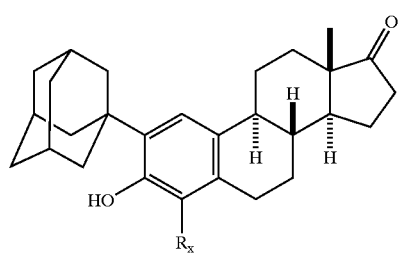

$R^x$ is not hydrogen.

2. The compound of claim 1, wherein said compound has the formula:

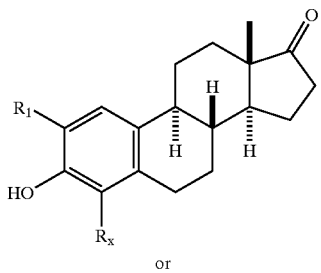

or

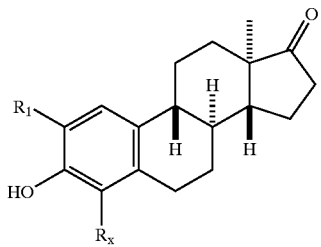

wherein R¹ and $R^x$ are as defined in claim 1.

3. The compound of claim 1 wherein R¹ is adamantyl and $R^x$ is hydrogen or methyl.

4. The compound of the claim 3 wherein the compound has the formula:

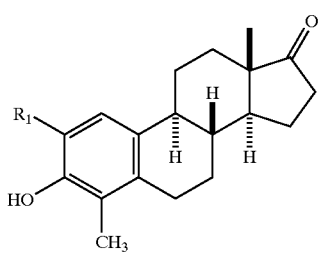

or the enantiomer thereof.

5. The compound of claim 3 wherein the compound has the formula:

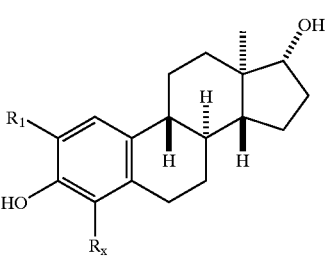

or the enantiomer thereof.

6. The compound of claim 1 wherein said compound has the formula:

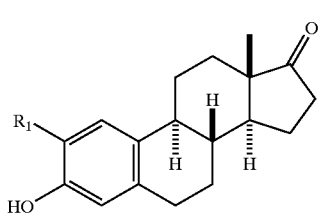

-continued or

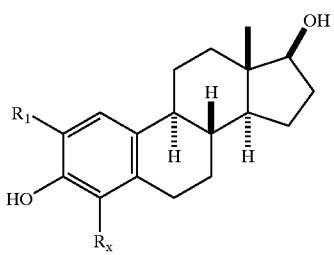

wherein R¹ and $R^x$ are as defined in claim 1.

7. The compound of claim 6 wherein R¹ is adamantyl and $R^x$ is hydrogen, methyl or methylpropyl.

8. The compound of claim 7 wherein the compound has the formula:

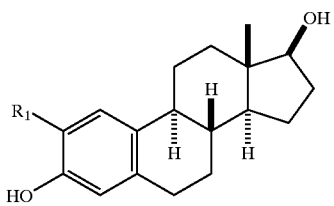

or the enantiomer thereof.

9. The compound of claim 7 wherein the compound has the formula.

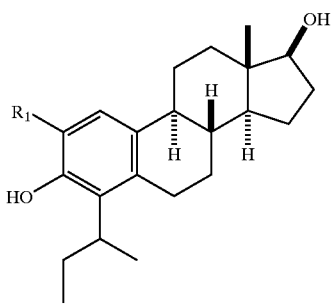

or the enantiomer thereof.

10. The compound of claim 3 wherein the compound has the formula:

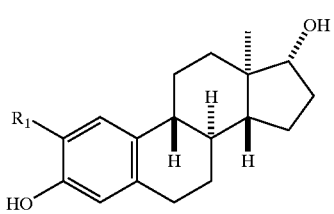

or the enantiomer thereof.

11. The compound of claim 1 wherein the bridged structure is bicyclic, tricyclic or tetracyclic.

12. The compound of claim 11 wherein said structure is selected from the group consisting of: bicyclo[1.1.0]butanyl; bicyclo[2.2.1]heptanyl; bicyclo[3.2.1]octanyl; bicyclo[4.3.2] nonanyl; bicyclo[4.3.2]undecanyl; tricyclo[2.2.1.0¹] heptanyl; tricyclo[5.3.1.1¹]dodecanyl; tricyclo[3.3.1.13,7] decanyl; tricyclo[5.4.0.0$^{2,9}$]undecanyl; and, tricyclo [5.3.2.0$^{4,9}$]dodecanyl.

13. The compound of claim 12 wherein said structure is selected from the group consisting of: tricyclo[2.2.1.0$^1$]heptanyl; tricyclo[5.3.1.1$^1$]dodecanyl: tricyclo[3.3.1.13,7]decanyl; tricyclo[5.4.0.0$^{2,9}$]undecanyl; and, tricyclo[5.3.2.0$^{4,9}$]dodecanyl.

14. The compound of claim 13 wherein said structure is tricyclo[3.3.1.13,7]decanyl.

15. A compound having the formula:

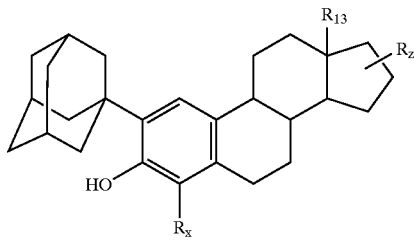

wherein: R$^x$ is substituted or unsubstituted alkyl; R$^{13}$ is hydrogen or substituted or unsubstituted alkyl; and, R$^z$ is hydrogen, hydroxy, substituted or unsubstituted alkyl, or oxo.

16. The compound of claim 15 wherein R$^z$ is oxo.

17. The compound of claim 16 wherein said compound has the structure:

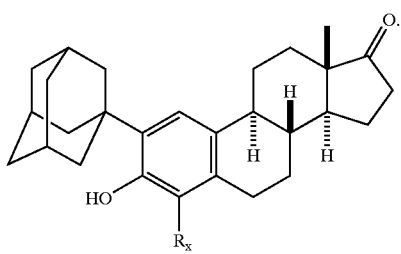

18. The compound of claim 17 wherein R$^x$ is substituted alkyl.

19. The compound of claim 17 wherein R$^x$ is unsubstituted alkyl.

20. A compound having having the formula:

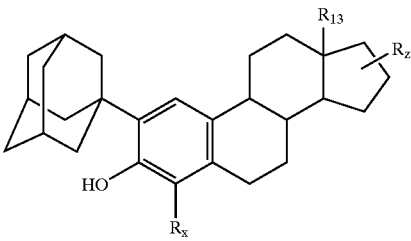

wherein: R$^x$ is selected from the group consisting of hydrogen and substituted or unsubstituted alkyl; R$^{13}$ is hydrogen or substituted or unsubstituted alkyl; and, R$^z$ is hydrogen, hydroxy, or substituted or unsubstituted alkyl.

21. The compound of claim 20 wherein R$^z$ is hydroxy.

22. The compound of claim 21 wherein said compound has the structure:

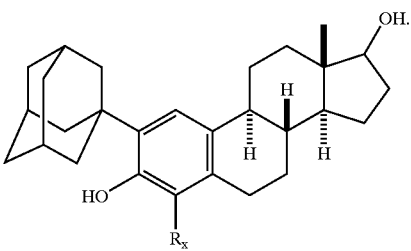

23. The compound of claim 22 wherein R$^x$ is substituted alkyl.

24. The compound of claim 22 wherein R$^x$ is unsubstituted alkyl.

25. The compound of claim 22 wherein R$^x$ is hydroxy.

* * * * *